(12) United States Patent
Martin

(10) Patent No.: US 9,675,569 B2
(45) Date of Patent: *Jun. 13, 2017

(54) METHOD FOR TREATING A PULMONARY DISEASE STATE IN MAMMALS BY UP REGULATING INDIGENOUS IN VIVO LEVELS OF INFLAMMATORY AGENTS IN MAMMALIAN CELLS

(76) Inventor: Alain Martin, Flemington, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/398,603

(22) PCT Filed: Jun. 13, 2012

(86) PCT No.: PCT/US2012/042254
§ 371 (c)(1),
(2), (4) Date: Feb. 5, 2015

(87) PCT Pub. No.: WO2013/187891
PCT Pub. Date: Dec. 19, 2013

(65) Prior Publication Data
US 2016/0022616 A1  Jan. 28, 2016

(51) Int. Cl.

| | | |
|---|---|---|
| A61K 31/19 | (2006.01) |
| A61K 38/28 | (2006.01) |
| A61K 31/465 | (2006.01) |
| A61K 45/06 | (2006.01) |
| A61K 31/7056 | (2006.01) |
| A61K 31/351 | (2006.01) |
| A61K 47/12 | (2006.01) |
| A61K 31/56 | (2006.01) |
| A61K 31/58 | (2006.01) |
| A61K 38/19 | (2006.01) |
| A61K 35/15 | (2015.01) |
| A61K 31/522 | (2006.01) |
| A61K 9/00 | (2006.01) |
| A61K 9/12 | (2006.01) |
| A61M 15/00 | (2006.01) |

(52) U.S. Cl.
CPC ............ *A61K 31/19* (2013.01); *A61K 9/0043* (2013.01); *A61K 9/0078* (2013.01); *A61K 31/351* (2013.01); *A61K 31/465* (2013.01); *A61K 31/522* (2013.01); *A61K 31/56* (2013.01); *A61K 31/58* (2013.01); *A61K 31/7056* (2013.01); *A61K 35/15* (2013.01); *A61K 38/19* (2013.01); *A61K 38/28* (2013.01); *A61K 45/06* (2013.01); *A61K 47/12* (2013.01); *A61K 9/0056* (2013.01); *A61K 9/12* (2013.01); *A61M 15/009* (2013.01)

(58) Field of Classification Search
None
See application file for complete search history.

(56) References Cited

U.S. PATENT DOCUMENTS

| | | | | |
|---|---|---|---|---|
| 6,689,810 B2* | 2/2004 | Martin | ................. | A61K 31/19 |
| | | | | 514/492 |
| 8,114,907 B2* | 2/2012 | Martin | ................. | A61K 31/19 |
| | | | | 514/557 |
| 2009/0041739 A1* | 2/2009 | Martin | ................. | A61K 31/19 |
| | | | | 424/94.1 |

OTHER PUBLICATIONS

Rennard et al. Smoking Cessation. Chest 2000; 117:360S-364S.*

* cited by examiner

*Primary Examiner* — Satyanarayana R Gudibande
*Assistant Examiner* — Jia-Hai Lee
(74) *Attorney, Agent, or Firm* — Craig M Bell; Bell IP Law

(57) ABSTRACT

The present invention provides novel methods for treating a pulmonary disease state in mammals by up-regulating indigenous in vivo levels of an inflammatory agent in mammalian cells comprising contacting the mammalian cells with a therapeutically effective amount of an inflammatory regulator and a pharmaceutical agent. The inflammatory agent is selected from the group consisting of cytokines, transforming growth factor-β, elastase, and white blood cells, and wherein the inflammatory regulator is selected from the group consisting of pyruvates and pyruvate precursors. The pharmaceutical agent is selected from the group comprising anti-bacterial agents, anti-virals, anti-fungals, anti-tumors, antihistamines, proteins, enzymes, hormones such as insulin, non-steroidal anti-inflammatories, cytokines, steroids, and nicotine.

7 Claims, 10 Drawing Sheets

Individual sputum total protein levels before and after study drug inhalation. Slash marks represent the median level.

Median change from pre- to post-study drug inhalation in sputum total protein levels and by drug dose level.

Individual sputum free elastase levels before and after study drug inhalation

Median change from pre- to post-study drug inhalation in sputum free elastase levels and by drug dose level Individual sputum IL-6 levels before and after study drug inhalation. Slash marks represent the median level.

Median change from pre- to post-study drug inhalation in sputum IL-6 levels and by drug dose level.

Individual sputum IL-8 levels before and after study drug inhalation.

Median change from pre- to post-study drug inhalation in sputum IL-8 levels and by drug dose level.

Individual sputum TNF-α levels before and after study drug inhalation. Slash marks represent the median level.

Median change from pre- to post-study drug inhalation in sputum TNF-α levels and by drug dose level.

METHOD FOR TREATING A PULMONARY DISEASE STATE IN MAMMALS BY UP REGULATING INDIGENOUS IN VIVO LEVELS OF INFLAMMATORY AGENTS IN MAMMALIAN CELLS

CROSS-REFERENCE TO RELATED APPLICATIONS

The present application is a national phase entry under 35 U.S.C. §371 of International Application No. PCT/US2012/042254 filed Jun. 13, 2012, which claims the benefit of priority of a continuation-in-part application Ser. No. 12/009,649 filed 22 Jan. 2008 which is a continuation-in-part application of U.S. patent application Ser. No. 11/890,911, filed 8 Aug. 2007 now U.S. Pat. No. 8,114,907 to Martin, the disclosures of which are incorporated herein by reference.

FIELD OF THE INVENTION

The present invention provides novel methods for treating a pulmonary disease state in mammals by up regulating indigenous in vivo levels of an inflammatory agent in mammalian cells comprising contacting the mammalian cells with a therapeutically effective amount of an inflammatory regulator, wherein the inflammatory agent is selected from the group consisting of cytokines, transforming growth factor-β, elastase, and white blood cells, and wherein the inflammatory regulator is selected from the group consisting of pyruvates and pyruvate precursors.

BACKGROUND OF THE INVENTION

The disclosures referred to herein to illustrate the background of the invention and to provide additional detail with respect to its practice are incorporated herein by reference and, for convenience, are referenced in the following text and respectively grouped in the appended bibliography.

Inflammatory agents are produced by a wide variety of body cells and are natural proteins produced by the cells of the immune system of most vertebrates in response to challenges by foreign agents such as viruses, bacteria, parasites, and tumor cells (1). There are many physiological disease states in man wherein the human body's immune system produces abnormally low levels of inflammatory agents. In these conditions, the body needs an inflammatory regulator to increase or up-regulate specific inflammatory agents to fight infections in the lungs and sinuses and/or to enhance a balanced immune system. Diseases of the human body that results in the production of abnormally low inflammatory agents including IL-10, include HIV, Humoral Immune Deficiency, Alzheimer's, Interstitial lung disease, Sarcoidosis, Cystic Fibrosis, T-cell deficiency, Neutropenia, Asplenia, complement deficiency, allergic Rhinitis, sinusitis, COPD, Asthma. All of these diseases result in the body incurring an imbalance to the immune system that leads to high rates of infections, including infections in the sinuses and lungs.

There are also medications and drugs that once administered, lower the body's own immune systems inflammatory agents which results in the eventual onset of infections and injury to normal cells and membranes. These drugs include steroids, cancer drugs, alkylating agents, anti-metabolites, Azathioprine and mercaptopurine (immunosuppressive agents) antibiotics, antibodies, cyclosporine, sirolimus, nicotine, and insulin. Other irritants like chemicals, irritant gases such as inhaled diesel fumes and cigarette smoke also lower certain inflammatory agents of the immune system needed to maintain a healthy immune system in the lungs and sinuses.

When inflammation is activated, many inflammatory cytokines become elevated, while other components of the immune system become suppressed, causing an imbalance in the immune system, that can injure cells and organs. The present invention comprises compositions and methods that bring balance back to the immune system. When certain inflammatory agents are abnormally high, the levels of other inflammatory agents are reduced or shut down. It is at this point, that the use of an inflammatory regulator is appropriate to up-regulate these reduced inflammatory agents and bring a necessary balance back to the immune system, allowing it to properly fight infections and prevent tissue damage. It has been been surprisingly discovered that high levels of inhaled pyruvate enhance the up-regulation of depressed levels of certain cytokines that have been lowered by the increased production of others so as to balance the negative effects of the other elevated cytokines and allows the immune system to function properly to fight infections and decrease the likelihood of tissue damage that may result from the swelling and fluid imbalance in cells. For example, IL-10 is capable of inhibiting the synthesis of pro-inflammatory cytokines and also displays a potent ability to suppress an antigen induced reaction. Therefore, up-regulating IL-10 has been shown to be effective in treating allergic rhinitis in the following examples.

Cytokines are a group of proteins and peptides that are used in organisms as signaling compounds and are used to allow one cell to communicate with another. The cytokine family consists mainly of smaller water-soluble proteins and glycoproteins. Cytokines are released by many types of cells, principally activated lymphocytes, and macrophages but also endothelium, epithelium and connective tissue. They are particularly important in both innate and adaptive immune responses. Due to their central role in the immune system, cytokines are involved in a variety of immunological, inflammatory and infectious diseases.

Interleukins (Ls) are a group of inflammatory cytokines that were first seen to be expressed by white blood cells. Interleukins are produced by a wide variety of bodily cells including endothelial cells and macrophages. The family of interleukins includes IL-1 to IL-33. The function of the immune system depends in a large part on interleukins, and rare deficiencies of a number of them have been described, all featuring autoimmune diseases or immune deficiency.

Interferons (IFNs) belong to a large class of glycoproteins and are cytokines. Interferons are natural proteins produced by the cells of the immune system of most vertebrates in response to challenges by foreign agents such as viruses, bacteria, parasites and tumor cells. Interferons assist the immune response by inhibiting viral replication within other cells of the body.

Tumor necrosis factor (TNF) is a cytokine involved in systemic inflammation and is a member of a group of cytokines that stimulate the acute phase reaction. Tumor necrosis factor causes apoptotic cell death, cellular proliferation, differentiation, inflammation, tumorigenesis, and viral replication. Tumor necrosis factors primary role is in the regulation of immune cells. Dysregulation and, in particular, overproduction of tumor necrosis factor have been implicated in a variety of human diseases, as well as cancer Chemokines are a family of small cytokines, or proteins that are classified according to shared structural characteristics such as small size (they are all approximately 8-10 kilo Daltons in size), and the presence of four cysteine residues in conserved locations that are key to forming their 3-dimensional shape. Chemokines have the ability to induce directed chemotaxis in nearby responsive cells (chemotactic cytokines). Some chemokines are considered pro-inflammatory and can be induced during an immune response to promote cells of the immune system to a site of infection, while others are considered homeostatic and are involved in controlling the migration of cells during normal processes of tissue maintenance or development. Chemokines exert their biological effects by interacting with G protein-linked transmembrane receptors called chemokine receptors that are selectively found on the surfaces of their target cells.

Cytokines and chemokines have the ability to stimulate leukocyte movement and play an important role in inflammation. Cytokines can influence the synthesis of other cytokines and chemokines. Cytokines can also stimulate cell proliferation acting as growth factors. Cytokines that regulate lymphocyte activation, growth and differentiation include IL-2, IL-4, IL-10, and TNF-β. Cytokines involved with natural immunity, inflammation, include TNF-α, IL-1, INF-α, INF-β, and IL-6. Cytokines that activate inflammatory cells like macrophages include IFN-γ, TNF-α, TNF-β, IL-5, IL-10, IL-12, and IL-8. Cytokines that stimulate hemopoiesis and mediate immature leukocyte growth and differentiation include IL-3, IL-7, c-kit ligand, granulocyte-macrophage, granulocyte colony-stimulating factor (G-CSF), and stem cell factor. Granulocyte colony-stimulating factor is a glycoprotein, growth factor or cytokine produced by a number of different tissues to stimulate the bone marrow to produce granulocytes and stem cells. Granulocyte colony-stimulating factor then stimulates the bone marrow to pulse them out of the marrow into the blood.

IL-8 is responsible in attracting white blood cells to the site of infection. The major cytokines that mediate inflammation are IL-1, IL-8, and TNF (α and β). IL-1 and TNF-α are produced by activated macrophages. Their secretion can be stimulated by infections, endotoxins, immune complexes, toxins, physical injury, and a variety of inflammatory processes. Their most important actions in inflammation are their effect on endothelium, leukocytes, and fibroblasts and induction of the systemic acute phase reactions. TNF also cause aggregation and priming of neutrophils, leading to a release of proteolytic enzymes, thus contributing to tissue damage. TNF-α, IL-1, and IL-6 also induce the systemic acute phase responses associated with infection, or injury, including fever, loss of appetite, the production of slow wave sleep, release of neutrophils into circulation, release of hormones, hemodynamic effects of septic shock, hypotension, decrease in vascular resistance, increased heart rate, and decrease in blood pH.

An excess of inflammatory agents can increase the production of oxygen radicals, including superoxide anions and hydrogen peroxide, produced during the inflammatory phase of an injury, which will destroy healthy tissue surrounding the site and will mitigate the positive bronchodilation effect of nitric oxide (26). Oxygen radicals can also initiate lipid peroxidation employing arachidonic acid as a substrate producing prostaglandins and leukotrienes. Hydrogen peroxide ($H_2O_2$) can induce arachidonic acid metabolism in alveolar macrophages. Oxygen radicals also produce 8-isoprostanes, which are potent renal and pulmonary artery vasoconstrictors, bronchoconstrictors, and induce airflow obstructions (26, 27). Because oxygen radicals contribute to the instability of nitric oxide, the addition of superoxide dismutase (SOD) or catalase (15) or Vitamin E (28) protect nitric oxide to produce its desired bronchodilation (2).

Hydrogen peroxide is elevated in patients with chronic obstructive pulmonary disease (COPD), asthma, and Acute Respiratory Distress Syndrome (ARDS) (26). A study in 28 patients showed a significant correlation between oxygen radical generation in white blood cell count (WBC) and the degree of bronchial hyperreactivity in vivo in non-allergic patients (18). Thus the ability of pyruvate to regulate inflammation, and inflammatory agents, which can increase the synthesis of oxygen radicals, should reduce the production of oxygen radicals when needed.

Sodium pyruvate is an antioxidant that reacts directly with oxygen radicals to neutralize them. In macrophages, and other cell lines, sodium pyruvate regulates the level of oxygen radicals by acting as an antioxidant and also increases the synthesis of nitric oxide (9). It can specifically lower the overproduction of superoxide anions. Sodium pyruvate also increases cellular levels of glutathione, a major cellular antioxidant (12). It was recently discovered that glutathione is reduced dramatically in antigen-induced asthmatic patients (13) and inhaled glutathione does not readily enter cells. Pyruvate does enter all cells via a transport system and can also cross the blood brain barrier. Excess sodium pyruvate beyond that needed to neutralize oxygen radicals will enter the bronchial and lung cells. All cells have a transport system that allow cells to concentrate pyruvate at higher concentrations than serum levels. In the cell, pyruvate raises the pH level, increases levels of ATP, decreasing levels of ADP and cAMP, and increases levels of GTP, while decreasing levels of cGMP. Nitric oxide (NO) acts in the opposite mode by increasing levels of cGMP and ADP, and requires an acidic pH range in which to work (19). While the above therapeutic compositions and methods are reported to inhibit the production of reactive oxygen intermediates, like hydrogen peroxide or peroxynitrite, none of the disclosures describe methods for treating a pulmonary disease state in mammals by regulating indigenous in vivo levels of inflammatory agents in mammalian cells.

U.S. Pat. No. 6,063,407 (Zapol et al.) discloses methods of treating, inhibiting or preventing vascular thrombosis or arterial restenosis in a mammal. The methods include causing the mammal to inhale a therapeutically effective concentration of gaseous nitric oxide. The inhaled nitric oxide may further comprise compounds that potentiate the beneficial effects of inhaled nitric oxide and antithrombotic agents that complement or supplement the beneficial effects of inhaled nitric oxide.

U.S. Pat. No. 6,020,308 (Dewhirst et al.) discloses the use of an inhibitor of nitric oxide activity, such as a nitric oxide scavenger or a nitric oxide synthase inhibitor, as an adjunct to treatment of inappropriate tissue vascularization disorders.

U.S. Pat. No. 5,891,459 (Cooke et al.) discloses the maintenance or improvement of vascular function and structure by long term administration of physiologically acceptable compounds, such as L-arginine, L-lysine, physiologically acceptable salts thereof, and polypeptide precursors thereof, which enhance the level of endogenous nitric oxide or other intermediates in the nitric oxide induced relaxation pathway in the host. The method further comprises the administration of other compounds, such as B6, folate, B12, or an antioxidant, which provide for short-term enhancement of nitric oxide.

U.S. Pat. No. 5,873,359 (Zapol et al.) discloses a method for treating or preventing bronchoconstriction or reversible pulmonary vasoconstriction in a mammal, which method includes causing the mammal to inhale a therapeutically effective concentration of gaseous nitric oxide or a therapeutically effective amount of a nitric oxide releasing compound and an inhaler device containing nitric oxide gas and/or a nitric oxide releasing compound.

U.S. Pat. No. 5,767,160 (Kaesemeyer) discloses a therapeutic mixture comprising L-arginine and an agonist of nitric oxide synthase, such as nitroglycerin for the treatment of diseases related to vasoconstriction. The vasoconstriction is relieved by stimulating the constitutive form of nitric oxide synthase (cNOS) to produce native nitric oxide. The native nitric oxide has superior beneficial effect when compared to exogenous nitric oxide produced by an L-arginine independent pathway in terms of the ability to reduce clinical endpoints and mortality.

U.S. Pat. No. 5,543,430 (Kaesemeyer) discloses a therapeutic mixture comprising a mixture of L-arginine and an agonist of nitric oxide synthase such as nitroglycerin for the treatment of diseases related to vasoconstriction. The vasoconstriction is relieved by stimulating the constitutive form of nitric oxide synthase to produce native nitric oxide. The native nitric oxide has superior beneficial effect when compared to exogenous nitric oxide produced by an L-arginine independent pathway in terms of the ability to reduce clinical endpoints and mortality.

U.S. Pat. No. 5,428,070 (Cooke et al.) discloses a method for treating atherogenesis and restenosis by long-term administration of physiologically acceptable compounds, which enhance the level of endogenous nitric oxide in the host. Alternatively, or in combination, other compounds may be administered which provide for short-term enhancement of nitric oxide, either directly or by physiological processes. In addition, cells may be genetically engineered to provide a component in the synthetic pathway to nitric oxide, so as drive the process to enhance nitric oxide concentration, particularly in conjunction with the administration of a nitric oxide precursor.

U.S. Pat. No. 5,286,739 (Kilbourn et al.) discloses an anti-hypotensive formulation comprising a mixture of amino acids, which is essentially arginine free or low in arginine (less than about 0.1%, most preferably, about 0.01%). The formulation may include ornithine, citrulline, or both. A method for prophylaxis and treatment of systemic hypotension in an animal is also provided. A method for treating hypotension caused by nitric oxide synthesis through administering a low or essentially arginine free parenteral formulation to an animal, so as to reduce or eliminate nitric oxide synthesis is described. A method for treating an animal in septic shock is also disclosed, comprising administering to the animal an anti-hypotensive formulation comprising a mixture of amino acids, which is essentially arginine free. Prophylaxis or treatment of systemic hypotension, particularly that hypotension incident to chemotherapeutic treatment with biologic response modifiers, such as tumor necrosis factor or interleukin-1 or 2, may be accomplished through the administration of the defined anti-hypotensive formulations until physiologically acceptable systolic blood pressure levels are achieved in the animal. Treatment of an animal for septic shock induced by endotoxin may also be accomplished by administering to the animal the arginine free formulations.

U.S. Pat. No. 5,217,997 (Levere et al.) discloses a method for treating a high vascular resistance disorder in a mammal by administering to a mammalian organism in need of such treatment a sufficient amount of L-arginine or pharmaceutically acceptable salt thereof to treat a high vascular resistance disorder. The L-arginine is typically administered in the range of about 1 mg to 1500 mg per day. High vascular resistance disorders include hypertension, primary or secondary vasospasm, angina pectoris, cerebral ischemia and preeclampsia. Also disclosed is a method for preventing or treating bronchial asthma in a mammal by administering to a mammalian organism in need of such prevention or treatment a sufficient amount of L-arginine to prevent or treat bronchial asthma.

U.S. Pat. No. 5,158,883 (Griffith) discloses pharmaceutically pure physiologically active NG-aminoarginine (i.e., the L or D, L form), or pharmaceutically acceptable salts thereof, administered in a nitric oxide synthesis inhibiting amount to a subject in need of such inhibition (e.g., a subject with low blood pressure or needing immunosuppressive effect) or added to a medium containing isolated organs, intact cells, cell homogenates or tissue homogenates in an amount sufficient to inhibit nitric oxide formation to elucidate or control the biosynthesis, metabolism or physiological role of nitric oxide.

U.S. Pat. Nos. 5,798,388, 5,939,459, and 5,952,384 (Katz) pertain to methods for treating various disease states in mammals caused by mammalian cells involved in the inflammatory response and compositions useful in the method. The method comprises contacting the mammalian cells participating in the inflammatory response with an inflammatory mediator. The inflammatory mediator is present in an amount capable of reducing the undesired inflammatory response and is an antioxidant. The preferred inflammatory mediator is a pyruvate. Katz discloses the treatment of airway diseases of the lungs such as bronchial asthma, acute bronchitis, emphysema, chronic obstructive emphysema, centrilobular emphysema, panacinar emphysema, chronic obstructive bronchitis, reactive airway disease, cystic fibrosis, bronchiectasis, acquired bronchiectasis, kartaagener's syndrome; atelectasis, acute atelectasis, chronic atelectasis, pneumonia, essential thrombocytopenia, legionnaires disease, psittacosis, fibrogenic dust disease, diseases due to organic dust, diseases due to irritant gases and chemicals, hypersensitivity diseases of the lung, idiopathic infiltrative diseases of the lungs and the like by inhaling pyruvate containing compositions.

U.S. Pat. No. 5,296,370 (Martin et al.) discloses therapeutic compositions for preventing and reducing injury to mammalian cells and increasing the resuscitation rate of injured mammalian cells. The therapeutic composition comprises (a) pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the resuscitation of injured mammalian cells.

U.S. Pat. No. 6,689,810 (Martin) discloses a therapeutic composition for treating pulmonary diseases states in mammals by altering indigenous in vivo levels of nitric oxide. The therapeutic composition consists of pyruvates, pyruvate precursors, $\alpha$-keto acids having four or more carbon atoms, precursors of $\alpha$-keto acids having four or more carbons, and the salts thereof.

U.S. Pat. No. 7,122,578 (Martin) discloses a therapeutic composition for treating topical diseases states and injuries in mammals involving injuries, which cause pain, erythema, swelling, crusting, ischemia, scarring, and excess white blood cell infiltration. The method involves the use of $\alpha$-keto acids to suppress inflammation.

WO 2006/086643 (Martin) discloses a non-pulmonary treatment of mammalian diseases and injuries caused by the over-expression of peroxynitrite.

While the above therapeutic compositions and methods are reported to inhibit the production of reactive oxygen intermediates, such as hydrogen peroxide, peroxynitrite or nitric oxide, none of the disclosures describe a method for treating a pulmonary disease state in mammals by altering indigenous in vivo levels of inflammatory agents.

SUMMARY OF THE INVENTION

The present invention provides novel methods for treating a pulmonary disease state in mammals by up regulating indigenous in vivo levels of an inflammatory agent in mammalian cells comprising contacting the mammalian cells with a therapeutically effective amount of an inflammatory regulator, wherein the inflammatory agent is selected from the group consisting of cytokines, transforming growth factor-β, elastase, and white blood cells, and wherein the inflammatory regulator is selected from the group consisting of pyruvates and pyruvate precursors.

DETAILED DESCRIPTION OF THE INVENTION

Figure 1:
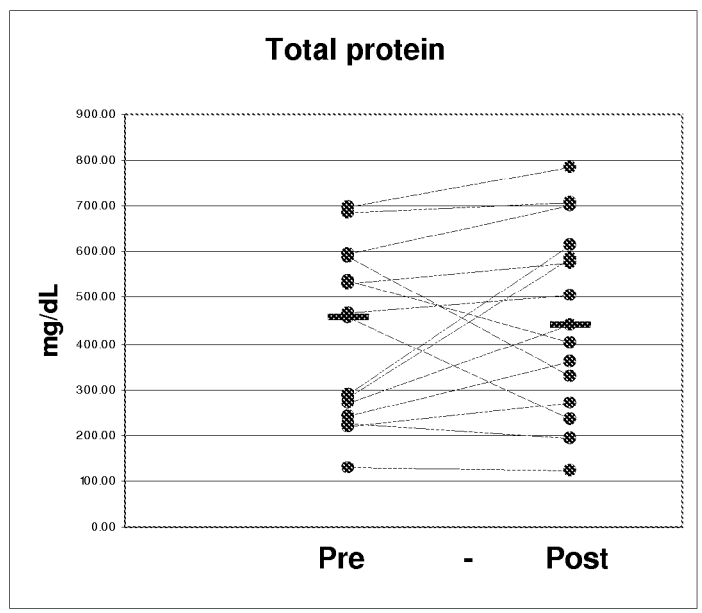
FIG. 1 is a graph illustrating individual sputum total protein levels before and after study drug inhalation. Slash marks represent the median level.

The present invention provides novel methods for treating a pulmonary disease state in mammals by up regulating indigenous in vivo levels of an inflammatory agent in mammalian cells comprising contacting the mammalian cells with a therapeutically effective amount of an inflammatory regulator, wherein the inflammatory agent is selected from the group consisting of cytokines, transforming growth factor-β, elastase, and white blood cells, and wherein the inflammatory regulator is selected from the group consisting of pyruvates and pyruvate precursors.

As used herein, the following terms have the given meanings:

The term "injured cell" as used herein refers to a cell which has some or all of the following: (a) injured membranes so that transport through the membranes is diminished and may result in one or more of the following, an increase in toxins and normal cellular wastes inside the cell and/or a decrease in nutrients and other components necessary for cellular repair inside the cell, (b) an increase in concentration of oxygen radicals inside the cell because of the decreased ability of the cell to produce antioxidants and enzymes, and (c) damaged DNA, RNA and ribosomes which must be repaired or replaced before normal cellular functions can be resumed.

The term "pharmaceutically acceptable," such as pharmaceutically acceptable carriers, excipients, etc., refers to pharmacologically acceptable and substantially non-toxic to the subject to which the particular compound is administered.

The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quaternary ammonium hydroxides, such as for example, tetramethylammonium hydroxide. Chemical modification of a pharmaceutical compound (i.e., drug) into a salt is a technique well known to pharmaceutical chemists to obtain improved physical and chemical stability, hydroscopicity, and solubility of compounds. See, e.g., H. Ansel et. al., Pharmaceutical Dosage Forms and Drug Delivery Systems ($6^{th}$ Ed. 1995) at pp. 196 and 1456-1457.

The term "prodrug" or "precursor" refers to compounds, which undergo biotransformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bio-reversible derivatives are used interchangeably. By inference, latentiation implies a time lag element or time component involved in regenerating the bioactive parent molecule in vivo. The term prodrug is general in that it includes latentiated drug derivatives as well as those substances, which are converted after administration to the actual substance, which combines with receptors. The term prodrug is a generic term for agents, which undergo biotransformation prior to exhibiting their pharmacological actions.

The term "therapeutically effective amount" refers to an amount of a therapeutically effective compound, or a pharmaceutically acceptable salt thereof, which is effective to treat, prevent, alleviate or ameliorate symptoms of a disease.

Pyruvates can act as inflammatory mediators (antioxidants) to neutralize oxygen radicals directly, thus lowering the level of inflammation. Pyruvates can also act as antioxidants to regulate the synthesis of nitric oxide. The regulation of oxygen radicals and the synthesis of nitric oxide operate by a different set of genes than those that regulate the synthesis of inflammatory agents such as cytokines and thus operates by a different mechanism. Applicant has discovered that pyruvates and pyruvate precursors can up or down regulate indigenous in vivo levels of inflammatory agents such as cytokines to regulate inflammation. Specifically, applicant has discovered that pyruvates in low dosage amounts, can down regulate the production of inflammatory agents and the number of white blood cells to stop the negative side effects of chronic inflammation in uninfected pulmonary diseases or, in high dosage amounts, can up-regulate the production of inflammatory agents and the number of white blood cells needed to kill infections or cancer in infected pulmonary diseases. Mediation of inflammation is very different from the regulation of inflammation. Mediation is a direct chemical effect on the inflammatory components such as the ability of pyruvates to act as antioxidants against oxygen radicals such as hydrogen peroxide, peroxynitrite, or nitric oxide to elicit a response. Regulation of inflammation, such as the up or down regulation of the levels of inflammatory agents, is a direct effect of pyruvates to elicit a response on a genetic level and to specifically effect and regulate the function of inflammatory cells such as white blood cells. The ability to regulate cellular functions of inflammatory cells is very different from the ability to directly chemically affect an oxygen radical. Both will lower inflammation, but only inflammatory regulators can up or down regulate the level of inflammation.

Pyruvates and pyruvate precursors control the positive and negative effects of inflammatory agents such as cytokines, transforming growth factor-β, elastase, and white blood cells at higher levels. Too high a number of white blood cells and other inflammatory agents are detrimental to lungs. Pyruvates and pyruvate precursors will lower and protect cells and organs from excess inflammatory agents and white blood cell numbers when they are high and infections are not involved. Moderate to severe asthmatics, emphysema patients, produce much higher levels of inflammatory agents including oxygen radicals especially in smokers and low dosages of pyruvates produce better results in these patients by lowering excess levels of inflammatory agents. The ability to control the levels of inflammation is important. Over production or under production is detrimental and produces various diseases in both the lungs and nasal cavities. Dosages of 5 ml of 0.5 mM pyruvates reduce the inflammatory markers in patients with lung diseases and can be used in diseases where inflammation is a problem, i.e., in smokers (21), mild asthmatics (21), in intubated or tracheostomized patients (19), in normal subjects after exercise and hyperventilation (21), COPD patients (22), and in patients with cystic fibrosis (22) with kartagener's syndrome (22), moderate or severe asthma (22), Sarcoidosis (22), and fibrosing alveolitis (22). Increased levels of inflammatory cytokines especially IL-8 which is a neutrophil activating cytokine, are chemotactic for eosinophils, which produce and enhance inflammation (20). Acute treatment with corticosteroids during an exacerbation of asthma is associated with a decline in inflammatory markers in adults and children (23).

In contrast, higher dosages of pyruvates can increase the number of white blood cells and the synthesis of cytokines needed in diseases where cytokines are abnormally low, such as in infections, cancer, and with the use of drugs. In all lung diseases, when inflammation is high, some cytokines are suppressed. Dosages of 5 ml of 5 mM pyruvates or higher beyond that needed to neutralize oxygen radicals will enter the bronchial and lung cells and increase the levels of white blood cells and IL-1, IL-6, IL-8, IL-10, TNF-α, and elastase to help fight infections and bring balance to the immune system. All cells have a transport system that allows cells to concentrate pyruvate at higher concentrations than serum levels. In the cell, pyruvate raises the pH level, increases levels of ATP, decreasing levels of ADP and cAMP, and increases levels of GTP, while decreasing levels of cGMP.

In summary, pyruvate enhances the body's ability to increase inflammatory agents to fight infections and tumors or to bring balance to the pulmonary or sinus immune system. During inflammation certain cytokines are elevated, whereas certain other cytokines are suppressed. The use of high levels of pyruvate alone or in combination with other drugs are effective for the treatment of lung diseases such as asthma, COPD and, in the treatment of tumors, bacterial infections, fungal infections, viral infections, angina, ischemic diseases, allergic rhinitis, sinusitis and congestive heart failure, where inflammatory agents and certain cytokines are low or suppressed.

The pulmonary diseases suitable for treatment by the cytokine regulators of the present invention include, but are not limited to, bronchial asthma, acute bronchitis, emphysema, chronic obstructive emphysema, chronic obstructive pulmonary disease, centrilobular emphysema, panacinar emphysema, chronic obstructive bronchitis, smokers disease, reactive airway disease, cystic fibrosis, bronchiectasis, acquired bronchiectasis, kartaagener's syndrome, acelectasis, acute atelectasis, chronic acelectasis, pneumonia, essential thrombocytemia, legionnaire's disease, psittacosis, fibrogenic dust disease, hypersensitivity diseases of the lung, idiopathic infiltrative diseases of the lungs, chronic obstructive pulmonary disorder, adult respiratory distress syndrome, pulmonary tumors, and diseases caused by organic dust, irritant gases, (Allergic Rhinitis, Sinusitis) and chemicals. Preferred disease states are cystic fibrosis, bronchial asthma, and chronic obstructive pulmonary disease, Allergic Rhinitis, and sinusitis.

The pulmonary tumors suitable for treatment by the cytokine regulators of the present invention include, but are not limited to, epidermoid (squamous cell) carcinoma, small cell (oat cell) carcinoma, adenocarcinoma, and large cell (anaplastic) carcinoma.

The inflammatory agent in the present invention may be selected from a wide variety of inflammatory agents. Preferred inflammatory agents are cytokines, transforming growth factor-β, elastase, and white blood cells. Preferred cytokines may be selected from the group consisting of interleukin-1, interleukin-2, interleukin-4, interleukin-6, interleukin-8, interleukin-10, interleukin-17, and interleukin-23. More preferred cytokines are interleukin-1, interleukin-6, interleukin-8 and interleukin 10. IL-10, IL-17, and IL-23 are all regulated by the levels of IL-6 and IL-8 and so regulation of IL-6 and IL-8 can regulate IL-10, IL-17, and IL-23.

Another preferred cytokine is tumor necrosis factor-α. Tumor necrosis factor-α is a cytokine involved in systemic inflammation and is a member of a group of cytokines that all stimulate the acute phase reaction.

Another preferred cytokine is interferon-α and interferon-β. Interferons are glycoproteins that assist the immune response by inhibiting viral replication within other cells of the body.

Another preferred inflammatory agent is transforming growth factor-β(TGF-β). Transforming growth factor-β regulates growth and proliferation of cells, blocking the growth of many different cell types including tumor cells.

Another preferred inflammatory agent is elastase. Elastase is an enzyme that digests and degrades a number of proteins including elastin, an elastic substance found in the lungs and other organs.

Another preferred inflammatory agent is white blood cells. White blood cells or leukocytes are cells of the immune system, which defend the body against both infectious disease and foreign materials. Several different and diverse types of leukocytes exist, however they are all produced and derived from a pluripotent cell in the bone marrow known as a hematopoietic stem cell. Leukocytes are found throughout the body, including the blood and lymphatic system.

The inflammatory regulators in the present invention are pyruvates and pyruvate precursors. Non-limiting illustrative examples of pyruvates include pyruvic acid, lithium pyruvate, sodium pyruvate, potassium pyruvate, magnesium pyruvate, calcium pyruvate, zinc pyruvate, manganese pyruvate, aluminum pyruvate, ammonium pyruvate, and mixtures thereof. Non-limiting illustrative examples of pyruvate precursors include pyruvyl-glycine, pyruvyl-alanine, pyruvyl-leucine, pyruvyl-valine, pyruvyl-isoleucine, pyruvyl-phenylalanine, pyruvamide, salts of pyruvic acid, and mixtures thereof.

The amount of the inflammatory regulator present in the therapeutic compositions of the present invention is a therapeutically effective amount. A therapeutically effective amount of the inflammatory regulator is that amount of the inflammatory agent necessary to treat the pulmonary disease. The exact amount of inflammatory regulator is a matter of preference subject to such factors as the type of inflammatory regulator being employed, the type of condition being treated as well as the other ingredients in the composition. The exact amount of inflammatory regulator will also be determined by whether the pulmonary disease is infected or uninfected. In general, the dosage of the inflammatory regulator may range from about 0.0001 mg to about 1 gram, preferably from about 0.001 mg to about 0.8 gram, and more preferably from about 0.01 mg to about 0.6 gram.

In another embodiment, the pyruvate or pyruvate precursor inflammatory regulator further may further comprise α-keto-isovaleric acid, or a precursor thereof. In general, the dosage of α-keto-isovaleric acid may range from about 0.0001 mg to about 1 gram, preferably from about 0.001 mg to about 0.8 gram, and more preferably from about 0.01 mg to about 0.6 gram.

In one embodiment, the level of inflammatory agents in the mammalian cells is abnormally low in the disease state. In another embodiment, the level of inflammatory agents in the mammalian cells is abnormally high in the disease state. Whether the levels of inflammatory agents that are abnormally low or abnormally high can be determined from the level of inflammatory agents in a patient's lungs and sputum.

In many cases, pulmonary diseases produce infections that these inflammatory regulators can treat. Such infections may be bacterial, viral, or fungal. The inflammatory regulators may be inhaled first to regulate inflammatory agents followed by inhalation of a therapeutic agent. The therapeutic agent may be administered prior to, concomitantly with, or after administration of the inflammatory regulator. The therapeutic agent may be selected from the group consisting of antibacterials, antivirals, antifungals, antitumors, antihistamines, proteins, enzymes, hormones, nonsteroidal anti-inflammatories, cytokines, nicotine, insulin, and steroids. All these therapeutic agents elicit an immune response, which will cause a suppression of certain cytokines.

The antibacterial agents which may be employed in the therapeutic compositions may be selected from a wide variety of water-soluble and water-insoluble drugs, and their acid addition or metallic salts, useful for treating pulmonary diseases. Both organic and inorganic salts may be used provided the antibacterial agent maintains its medicament value. The antibacterial agents may be selected from a wide range of therapeutic agents and mixtures of therapeutic agents, which may be administered in sustained release or prolonged action form. Nonlimiting illustrative specific examples of antibacterial agents include bismuth containing compounds, sulfonamides; nitrofurans, metronidazole, tinidazole, nimorazole, benzoic acid; aminoglycosides, macrolides, penicillins, polypeptides, tetracyclines, cephalosporins, chloramphenicol, and clindamycin. Preferably, the antibacterial agent is selected from the group consisting of bismuth containing compounds, such as, without limitation, bismuth aluminate, bismuth subcitrate, bismuth subgalate, bismuth subsalicylate, and mixtures thereof; the sulfonamides; the nitrofurans, such as nitrofurazone, nitrofurantoin, and furozolidone; and miscellaneous antibacterials such as metronidazole, tinidazole, nimorazole, and benzoic acid; and antibiotics, including the aminoglycosides, such as gentamycin, neomycin, kanamycin, and streptomycin; the macrolides, such as erythromycin, clindamycin, and rifamycin; the penicillins, such as penicillin G, penicillin V, Ampicillin and amoxicillin; the polypeptides, such as bacitracin and polymyxin; the tetracyclines, such as tetracycline, chlorotetracycline, oxytetracycline, and doxycycline; the cephalosporins, such as cephalexin and cephalothin; and miscellaneous antibiotics, such as chloramphenicol, and clindamycin. More preferably, the antibacterial agent is selected from the group consisting of bismuth aluminate, bismuth subcitrate, bismuth subgalate, bismuth subsalicylate, sulfonamides, nitrofurazone, nitrofurantoin, furozolidone, metronidazole, tinidazole, nimorazole, benzoic acid, gentamycin, neomycin, kanamycin, streptomycin, erythromycin, clindamycin, rifamycin, penicillin G, penicillin V, Ampicillin amoxicillin, bacitracin, polymyxin, tetracycline, chlorotetracycline, oxytetracycline, doxycycline, cephalexin, cephalothin, chloramphenicol, Mupericin and clindamycin.

The amount of antibacterial agent which may be employed in the therapeutic compositions of the present invention may vary depending upon the therapeutic dosage recommended or permitted for the particular antibacterial agent. In general, the amount of antibacterial agent present is the ordinary dosage required to obtain the desired result. Such dosages are known to the skilled practitioner in the medical arts and are not a part of the present invention. In a preferred embodiment, the antibacterial agent in the therapeutic composition is present in an amount from about 0.01% to about 10%, preferably from about 0.1% to about 5%, and more preferably from about 1% to about 3%, by weight.

The antiviral agents which may be employed in the therapeutic compositions may be selected from a wide variety of water-soluble and water-insoluble drugs, and their acid addition or metallic salts, useful for treating pulmonary diseases. Both organic and inorganic salts may be used provided the antiviral agent maintains its medicament value. The antiviral agents may be selected from a wide range of therapeutic agents and mixtures of therapeutic agents, which may be administered in sustained release or prolonged action form. Nonlimiting illustrative categories of such antiviral agents include RNA synthesis inhibitors, protein synthesis inhibitors, immunostimulating agents, protease inhibitors, and cytokines. Nonlimiting illustrative specific examples of such antiviral agents include the following medicaments.

(a) Acyclovir (9-[(2-hydroxyethyloxy)methyl]guanine, ZOVIRAX®) is a white, crystalline powder with a molecular weight of 225 Daltons and a maximum solubility in water of 2.5 mg/mL at 37° C. Acyclovir is a synthetic purine nucleoside analogue with in vitro and in vivo inhibitory activity against human herpes viruses including herpes simplex types 1 (HSV-1) and 2 (HSV-2), varicella-zoster virus (VZV), Epstein-Barr virus (EBV), and cytomegalovirus (CMV).

(b) Foscarnet sodium (phosphonoformic acid trisodium salt, FOSCAVIR) is a white, crystalline powder containing 6 equivalents of water of hydration with an empirical formula of $Na_3CO_6P_6H_2O$ and a molecular weight of 300.1. Foscarnet sodium has the potential to chelate divalent metal ions such as calcium and magnesium, to form stable coordination compounds. Foscarnet sodium is an organic analogue of inorganic pyrophosphate that inhibits replication of all known herpes viruses in vitro including cytomegalovirus (CMV), herpes simplex virus types 1 and 2 (HSV-1, HSV-2), human herpes virus 6 (HHV-6), Epstein-Barr virus (EBV), and varicella-zoster virus (VZV). Foscarnet sodium exerts its antiviral activity by a selective inhibition at the pyrophosphonate binding site on virus-specific DNA polymerases and reverse transcriptases at concentrations that do not affect cellular DNA polymerases.

(c) Ribavirin (1-β-D-ribofuranosyl-1,2,4-triazole-3-carboxamide, VIRAZOLE®) is a synthetic nucleoside which is a stable, white, crystalline compound with a maximum solubility in water of 142 mg/ml at 25° C. and with only a slight solubility in ethanol. The empirical formula is $C_8H_{12}N_4O_6$ and the molecular weight is 244.2 Daltons. Ribavirin has antiviral inhibitory activity in vitro against respiratory syncytial virus, influenza virus, and herpes simplex virus. Ribavirin is also active against respiratory syncytial virus (RSV) in experimentally infected cotton rats. In cell cultures, the inhibitory activity of Ribavirin for RSV is selective. The mechanism of action is unknown. Reversal of the in vitro antiviral activity by guanosine or xanthosine suggests Ribavirin may act as an analogue of these cellular metabolites.

(d) Vidarabine (adenine arabinoside, Ara-A, 9-β-D-arabinofuranosyladenine monohydrate, VIRA-A®) is a purine nucleoside obtained from fermentation cultures of *Streptomyces* antibiotics. Vidarabine is a white, crystalline solid with the empirical formula, $C_{10}H_{13}N_5O_4H_2O$. The molecular weight of vidarabine is 285.2, the solubility is 0.45 mg/ml at 25° C., and the melting point ranges from 260° C. to 270° C. Vidarabine possesses in vitro and in vivo antiviral activity against Herpes simplex virus types 1 and 2 (HSV-1 and HSV-2), and in vitro activity against varicella-zoster virus (VZV). The antiviral mechanism of action has not yet been established. Vidarabine is converted into nucleotides, which inhibit viral DNA polymerase.

(e) Ganciclovir sodium (9-(1,3-dihydroxy-2-propoxymethyl)guanine, monosodium salt, CYTOVENE®, CYMEVENE®) is an antiviral drug active against cytomegalovirus for intravenous administration. Ganciclovir sodium has a molecular formula of $C_9H_{12}N_6NaO_4$ and a molecular weight of 277.21. Ganciclovir sodium is a white lyophilized powder with an aqueous solubility of greater than 50 mg/mL at 25° C. Ganciclovir is a synthetic nucleoside analogue of 2'-deoxyguanosine that inhibits replication of herpes viruses both in vitro and in vivo. Sensitive human viruses include cytomegalovirus (CMV), herpes simplex virus-1 and -2 (HSV-1, HSV-2), Epstein-Barr virus (EBV), and varicella zoster virus (VZV).

(f) Zidovudine [azidothymidine (AZT), 3'-azido-3'-deoxythymidine, RETROVIR®] is an antiretroviral drug active against human immunodeficiency virus (HIV) for oral administration. Zidovudine is a white to beige, odorless, crystalline solid with a molecular weight of 267.24 Daltons and a molecular formula of $C_{10}H_{13}N_5O_4$. Zidovudine is an inhibitor of the in vitro replication of some retroviruses including HIV (also known as HTLV III, LAV, or ARV). Zidovudine is a thymidine analogue in which the 3'-hydroxy (—OH) group is replaced by an azido (—$N_3$) group.

(g) Phenol (carbolic acid) is a topical antiviral, anesthetic, antiseptic, and antipruritic drug. Phenol is a colorless or white crystalline mass, which is soluble in water, has a characteristic odor, a molecular formula of $C_6H_6O$, and a molecular weight of 94.11.

(h) Amantadine hydrochloride (1-adamantanamine hydrochloride, SYMMETREL®) has pharmacological actions as both an anti-Parkinson and an antiviral drug. Amantadine hydrochloride is a stable white or nearly, white crystalline powder, freely soluble in water and soluble in alcohol and in chloroform. The antiviral activity of amantadine hydrochloride against influenza A is not completely understood but the mode of action appears to be the prevention of the release of infectious viral nucleic acid into the host cell.

(i) Interferon α-n3 (human leukocyte derived, ALFERON®) is a sterile aqueous formulation of purified, natural, human interferon α proteins for use by injection. Interferon α-n3 injection consists of interferon α proteins comprising approximately 166 amino acids ranging in molecular weights from 16,000 to 27,000 Daltons. Interferons are naturally occurring proteins with both antiviral and antiproliferative properties.

(j) Interferon α-2a (recombinant, ROFERON-A®) is a sterile protein product for use by injection. Interferon α-2a is a highly purified protein containing 165 amino acids, and it has an approximate molecular weight of 19,000 Daltons. The mechanism by which Interferon α-2a, recombinant, exerts antitumor or antiviral activity is not clearly understood. However, it is believed that direct antiproliferative action against tumor cells, inhibition of virus replication, and modulation of the host immune response play important roles in antitumor and antiviral activity.

(k) Oseltamivir ((3R,4R,5S)-4-acetylamino-5-amino-3-(1-ethylpropoxy)-1-cyclohexene-1-carboxylic acid ethyl ester, TAMIFLU®) is a is an antiviral drug that is used in the treatment and prophylaxis of both influenza virus A and Influenza virus B. Oseltamivir is a neuraminidase inhibitor. It acts as a transition-state analogue inhibitor of influenza neuraminidase, preventing new viruses from emerging from infected cells. Oseltamivir has a molecular formula of $C_{16}H_{28}N_2O_4$.

Preferred antiviral agents to be employed may be selected from the group consisting of acyclovir, foscarnet sodium, Ribavirin, vidarabine, Ganciclovir sodium, zidovudine, phenol, amantadine hydrochloride, and interferon α-n3, interferon α-2a, and Oseltamivir. In a preferred embodiment, the antiviral agent is selected from the group consisting of acyclovir, foscarnet sodium, Ribavirin, vidarabine, and Ganciclovir sodium. In a more preferred embodiment, the antiviral agent is acyclovir.

The amount of antiviral agent which may be employed in the therapeutic compositions of the present invention may vary depending upon the therapeutic dosage recommended or permitted for the particular antiviral agent. In general, the amount of antiviral agent present is the ordinary dosage required to obtain the desired result. Such dosages are known to the skilled practitioner in the medical arts and are not a part of the present invention. In a preferred embodiment, the antiviral agent in the therapeutic composition is present in an amount from about 0.1% to about 20%, preferably from about 1% to about 10%, and more preferably from about 2% to about 7%, by weight.

The antifungal agents which may be employed in the therapeutic compositions may be selected from a wide variety of water-soluble and water-insoluble drugs, and their acid addition or metallic salts, useful for treating pulmonary diseases. Both organic and inorganic salts may be used provided the antifungal agent maintains its medicament value. The antifungal agents may be selected from a wide range of therapeutic agents and mixtures of therapeutic agents, which may be administered in sustained release or prolonged action form. Nonlimiting illustrative specific examples of antifungal agents include the following medicaments: miconazole, clotrimazole, tioconazole, terconazole, povidone-iodine, and butoconazole. Other antifungal agents are lactic acid and sorbic acid. Preferred antifungal agents are miconazole and clotrimazole.

The amount of antifungal agent, which may be employed in the therapeutic compositions of the present invention may vary depending upon the therapeutic dosage recommended or permitted for the particular antifungal agent. In general, the amount of antifungal agent present is the ordinary dosage required to obtain the desired result. Such dosages are known to the skilled practitioner in the medical arts and are not a part of the present invention. In a preferred embodiment, the antifungal agent in the therapeutic composition is present in an amount from about 0.05% to about 10%, preferably from about 0.1% to about 5%, and more preferably from about 0.2% to about 4%, by weight.

The antitumor agents which may be employed in the therapeutic compositions may be selected from a wide variety of water-soluble and water-insoluble drugs, and their acid addition or metallic salts, useful for treating pulmonary diseases. Both organic and inorganic salts may be used provided the antitumor agent maintains its medicament value. The antitumor agents may be selected from a wide range of therapeutic agents and mixtures of therapeutic agents, which may be administered in sustained release or prolonged action form. Nonlimiting illustrative specific examples include anti-metabolites, antibiotics, plant products, hormones, and other miscellaneous chemotherapeutic agents. Chemically reactive drugs having nonspecific action include alkylating agents and N-alkyl-N-nitroso compounds. Examples of alkylating agents include nitrogen mustards, azridines (ethylenimines), sulfonic acid esters, and epoxides.

Anti-metabolites are compounds that interfere with the formation or utilization of a normal cellular metabolite and include amino acid antagonists, vitamin and coenzyme antagonists, and antagonists of metabolites involved in nucleic acid synthesis such as glutamine antagonists, folic acid antagonists, pyrimidine antagonists, and purine antagonists. Antibiotics are compounds produced by microorganisms that have the ability to inhibit the growth of other organisms and include actinomycins and related antibiotics, glutarimide antibiotics, sarkomycin, fumagillin, streptonigrin, tenuazonic acid, actinogan, peptinogan, and anthracyclic antibiotics such as doxorubicin. Plant products include colchicine, podophyllotoxin, and *vinca* alkaloids. Hormones include those steroids used in breast and prostate cancer and corticosteroids used in leukemias and lymphomas. Other miscellaneous chemotherapeutic agents include urethane, hydroxyurea, and related compounds; thiosemicarbazones and related compounds; phthalanilide and related compounds; and triazenes and hydrazines. The anticancer agent may also be a monoclonal antibody or the use of X-rays. In a preferred embodiment, the anticancer agent is an antibiotic. In a more preferred embodiment, the anticancer agent is doxorubicin. In a most preferred embodiment, the anticancer agent is doxorubicin.

The amount of antitumor agent, which may be employed in the therapeutic compositions of the present invention may vary depending upon the therapeutic dosage recommended or permitted for the particular antitumor agent. In general, the amount of antitumor agent present is the ordinary dosage required to obtain the desired result. Such dosages are known to the skilled practitioner in the medical arts and are not a part of the present invention. In a preferred embodiment, the antitumor agent in the therapeutic composition is present in an amount from about 1% to about 50%, preferably from about 10% to about 30%, and more preferably from about 20% to about 25%, by weight.

The therapeutic agent of the present invention may also be a nasally administered steroid which when administered with pyruvate and/or one of the other α-keto acids provides immediate and long term systemic relief of allergic rhinitis, sinusitis and diseases caused by organic dust, irritant gases, and chemicals. Steroids useful in the practice of the present invention include those selected from the group consisting of fluticasone, (Flonase®), budesonide (Rhinocort®), beclomethasone, mometasone, flunisolide, triamcinolone and mixtures thereof. These may also be used in combination with an antihistamine. Suitable antihistamines are selected from the group consisting of pseudoephedrine, loratadine, fexofenadine, diphenhydramine, famodidine, ranitidine, citirazine, and other $H_1$ and $H_2$ antagonists. The anti-histamines may actually be administered singly and alone with the pyruvate compositions of the present invention in or together with the steroid for enhanced nasal relief.

Nicotine is an alkaloid found predominantly in tobacco and constitutes about 0.6-3% of tobacco by dry weight. Cigarette smoking which contains nicotine has been shown to suppress the immune system to cause infections and problems in the lungs and sinuses. In low concentrations, an average cigarette yields about 1.0 mg of absorbed nicotine. Nicotine acts as a stimulant in mammals and is one of the main factors responsible for the dependence-forming properties of tobacco smoking. Nicotine is a hygroscopic, oily liquid that is miscible with water in its base form. As a nitrogenous base, nicotine forms salts with acids that are usually solid and water-soluble. The primary therapeutic use of nicotine is in treating nicotine dependence in order to eliminate smoking with its health risks. In low concentrations, an average cigarette yields about 1.0 mg of absorbed nicotine. Nicotine acts as a stimulant in mammals and is one of the main factors responsible for the dependence-forming properties of tobacco smoking. Nicotine is a hygroscopic, oily liquid that is miscible with water in its base form. The primary therapeutic use of nicotine is in treating nicotine dependence in order to eliminate smoking with its health risks.

Insulin is an animal hormone, produced in the pancreas, whose presence informs the body's cells that the animal is well fed, causing liver and muscle cells to take in glucose and store it in the form of glycogen, and causing fat cells to take in blood lipids and turn them into triglycerides. Insulin is used medically to treat some forms of diabetes mellitus. Patients with type 1 diabetes mellitus depend on external insulin (most commonly injected subcutaneously) for their survival because of the absence of the hormone. Patients with type 2 diabetes mellitus have insulin resistance, relatively low insulin production, or both; some type 2 diabetics eventually require insulin when other medications become insufficient in controlling blood glucose levels.

Insulin is a peptide hormone composed of 51 amino acid residues. Insulin's genetic structure varies marginally between species of animal. Bovine insulin differs from human in only three amino acid residues, and porcine insulin in one. Even insulin from some species of fish is similar enough to human to be effective in humans. The C-peptide of proinsulin, however, is very divergent from species to species. All structures of insulin useful in humans, including synthetic "human" insulin, may be employed in the present invention. Unlike many medicines, insulin cannot be taken orally. Like nearly all proteins introduced into the gastrointestinal tract, insulin is degraded losing all insulin activity. Insulin is usually taken as subcutaneous injections or may be inhaled. The delivery of insulin by inhalation is not new. As with all insulin's, a patients' dosage must be adjusted for his/her particular situation. There are several ways to dose short-acting (rapid-acting) insulin. The following table outlines estimates of the recommended starting inhaled insulin dosages (based on body weight).

| Weight | Starting Inhaled Insulin Dose | Blisters |
| --- | --- | --- |
| 66 to 87 pounds | 1 mg per meal | One 1-mg blister |
| 88 to 132 pounds | 2 mg per meal | Two 1-mg blisters |
| 133 to 176 pounds | 3 mg per meal | One 3-mg blister |
| 177 to 220 pounds | 4 mg per meal | One 1-mg blister plus one 3-mg blister |
| 221 to 264 pounds | 5 mg per meal | Two 1-mg blisters plus one 3-mg blister |
| 265 to 308 pounds | 6 mg per meal | Two 3-mg blisters |

It was surprisingly and un-expectedly discovered that inhaling insulin with pyruvate reduced the irritation produced from insulin and produced better results than the use of insulin by itself. Diabetics that inhale insulin have difficulty if they have a pulmonary disease like COPD, which effects the dosage received. The addition of pyruvate enhanced insulin uptake for patients that have diabetes with pulmonary lung or upper respiratory sinus diseases.

Moreover, the inhalation of insulin is not only useful in the treatment of diabetes, but it can be used to treat Alzheimer's. In one patient with diabetes and mild Alzheimer's, the inhalation of insulin with pyruvate improved mental functions over the same concentration of inhaled insulin alone. It was discovered that inhaled pyruvate may increase IL-10 in the brain thus increases the efficacy of inhaled insulin, increasing cognitive functions in Alzheimer's patients. It has also been shown that certain immune system components when increased, enhances cognitive functions and decreased the amyloid protein, known to disrupt cognitive functions.

Obviously, numerous modifications and variations of the present invention are possible in the light of the above teachings and the invention is not limited to the examples herein. It is therefore understood that within the scope of the appended claims, the invention may be practiced otherwise than as specifically described herein. Throughout this application, various publications have been referenced. The disclosures in these publications are incorporated herein by reference in order to more fully describe the state of the art. The compounds of the present invention can be prepared according to the examples set out below. The examples are presented for purposes of demonstrating, but not limiting, the preparation of the compounds and compositions of this invention.

EXAMPLES

Example 1

Inhaled Sodium Pyruvate for the Treatment of Cystic Fibrosis Double Blind, Placebo-Controlled, Safety Study Sputum Inflammatory Biomarkers All of the enrolled and dosed subjects were able to provide sputum samples for analysis before and after exposure to study drug (sodium pyruvate for inhalation at 0.5, 1.5, and 5.0 mM levels). The subjects were given 5 ml samples to inhale. Specimens were of good quality for the planned assays.

The 0.5 mM levels of sodium pyruvate using 5 ml samples contain 0.28 mg of sodium pyruvate. The 5 mM levels of sodium pyruvate using 5 ml contain 2.8 mg of sodium pyruvate.

Samples were divided into two main aliquots after processing. The first aliquot was left untreated to be able to assay for the activity of free elastase. The second aliquot was treated with protease inhibitors pheylmethanesulfonylfluoride (PMSF) and ethylenediamine tetraacetic acid (EDTA) to stop any degradation of the cytokines of interest (IL-6, IL-8, IL-10, IL-17, and IL-23) and total protein.

For IL-10, IL-17 and IL-23, levels on sputum were at or below the limit of detection for the assays (7, 2 and 20 pg/mL respectively). For the other markers (total protein, elastase, IL-6, IL-8, TNF-α) levels detected where within those typically found in cystic fibrosis (CF) patients. Overall, significant changes were noted in these biomarkers tested in sputum by drug dose level or for the group as a whole (FIGS. 1-10).

Figure 2:
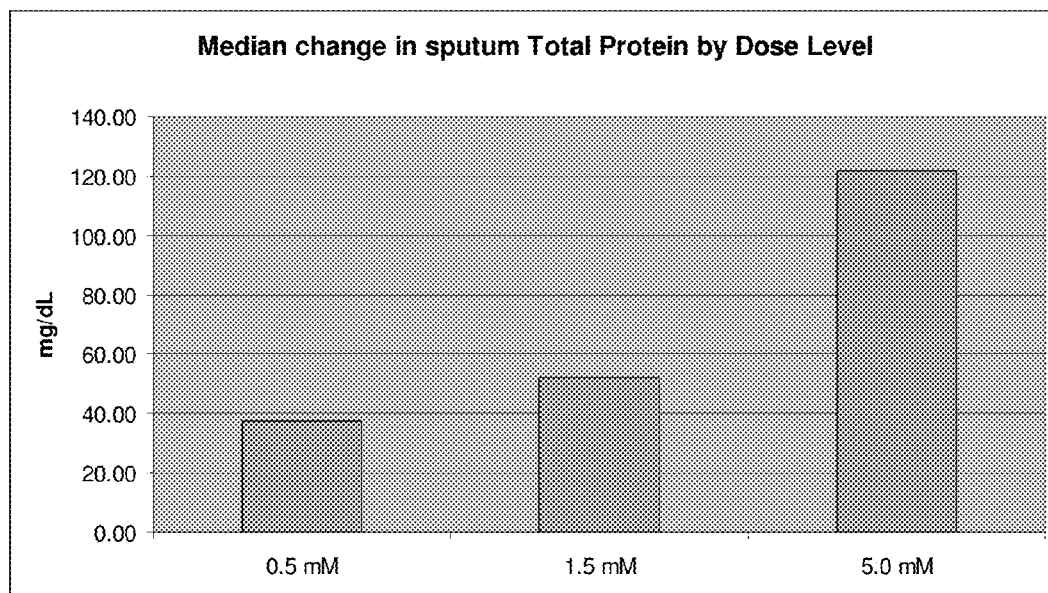
FIG. 2 is a graph illustrating median change from pre- to post-study drug inhalation in sputum total protein levels and by drug dose level.
Figure 3:
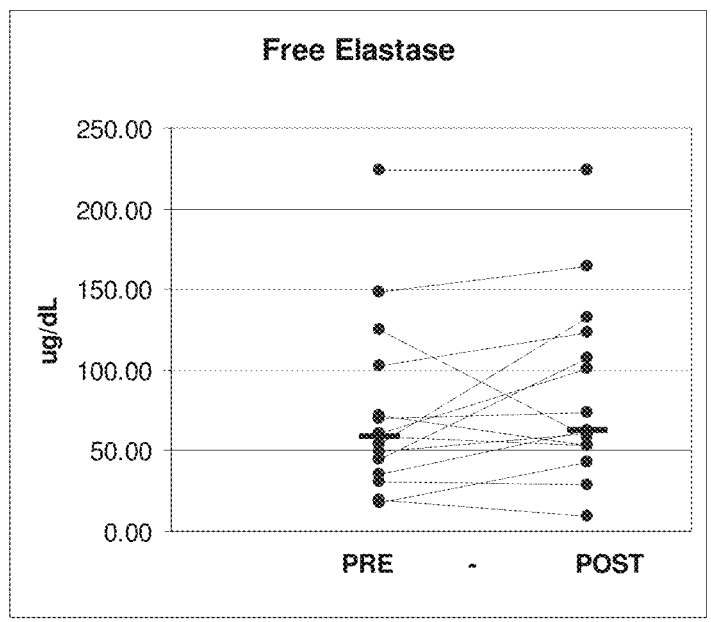
FIG. 3 is a graph illustrating individual sputum free elastase levels before and after study drug inhalation. Slash marks represent the median level.
Figure 4:
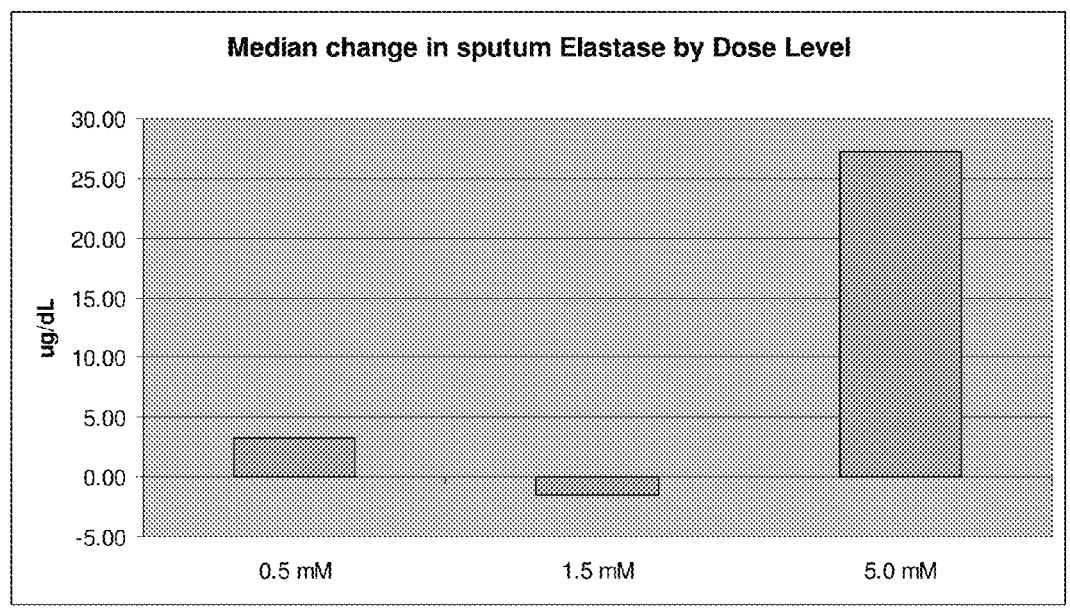
FIG. 4 is a graph illustrating median change from pre- to post-study drug inhalation in sputum free elastase levels and by drug dose level.
Figure 5:
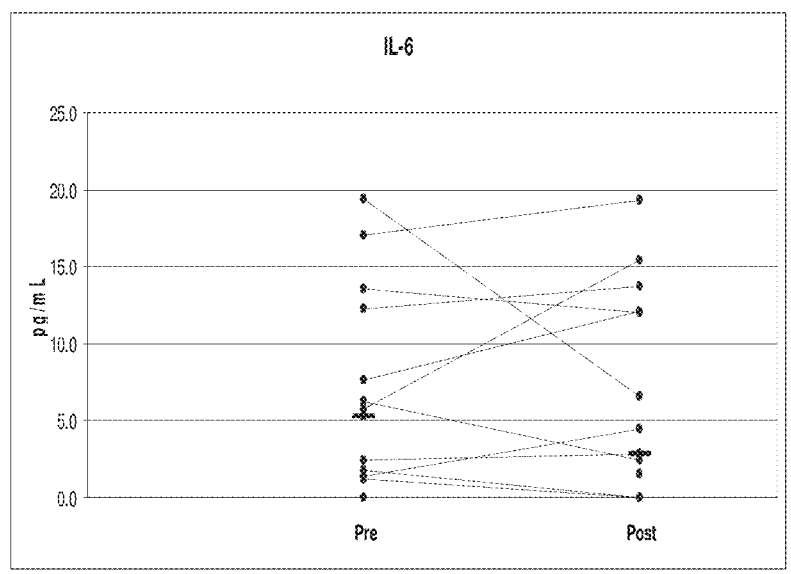
FIG. 5 is a graph illustrating individual sputum IL-6 levels before and after study drug inhalation. Slash marks represent the median level.
Figure 6:
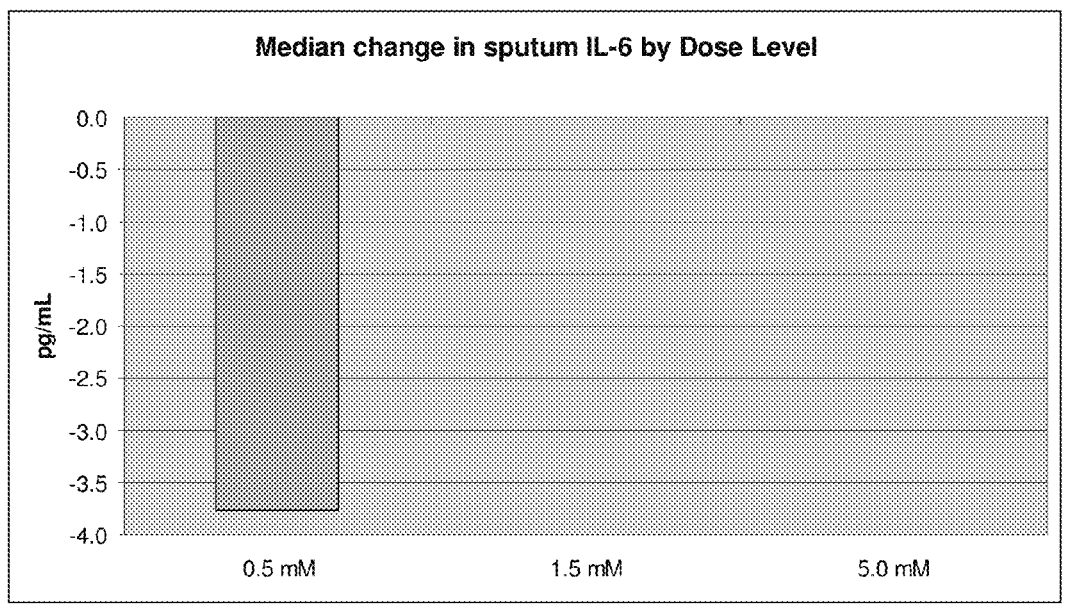
FIG. 6 is a graph illustrating median change from pre- to post-study drug inhalation in sputum IL-6 levels and by drug dose level.
Figure 7:
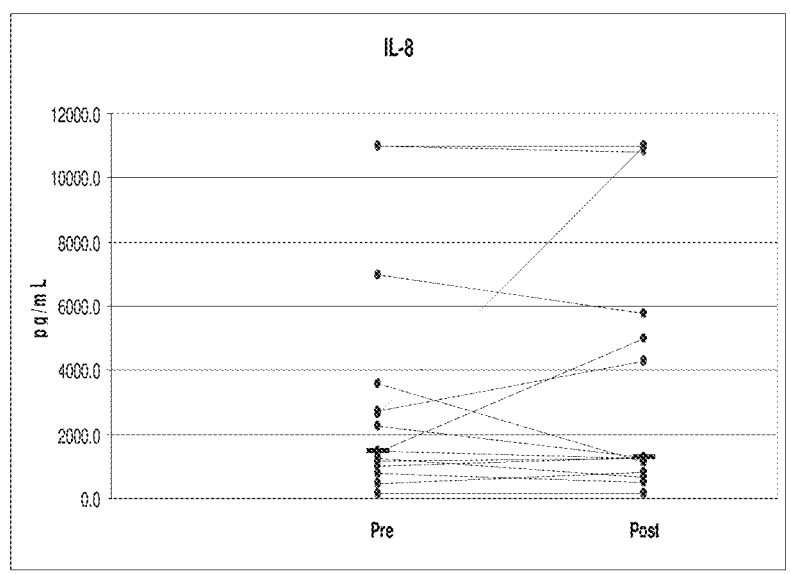
FIG. 7 is a graph illustrating individual sputum IL-8 levels before and after study drug inhalation. Slash marks represent the median level.
Figure 8:
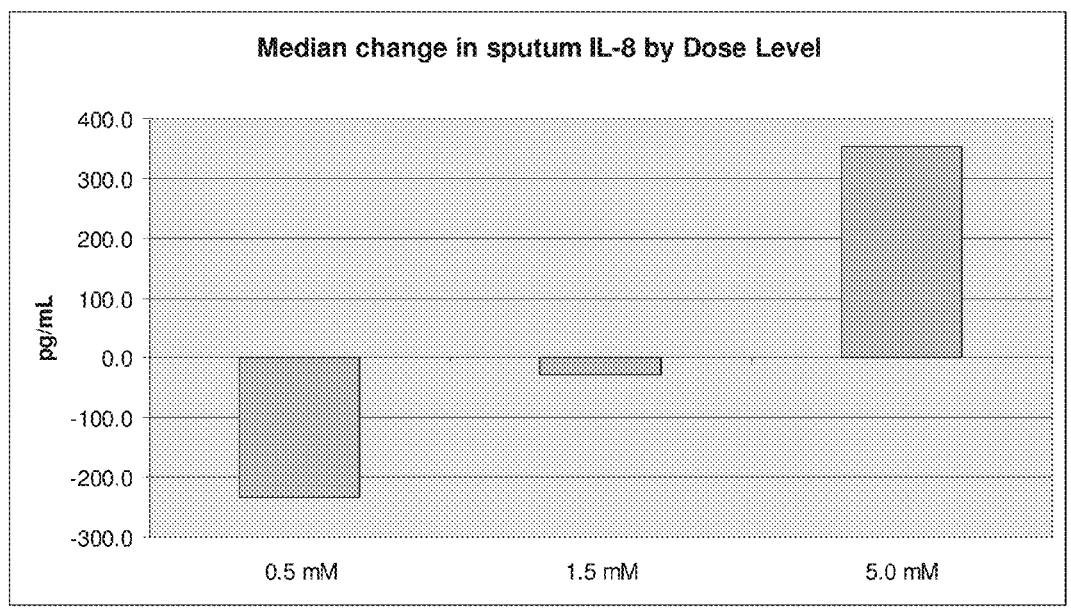
FIG. 8 is a graph illustrating median change from pre- to post-study drug inhalation in sputum IL-8 levels and by drug dose level.
Figure 9:
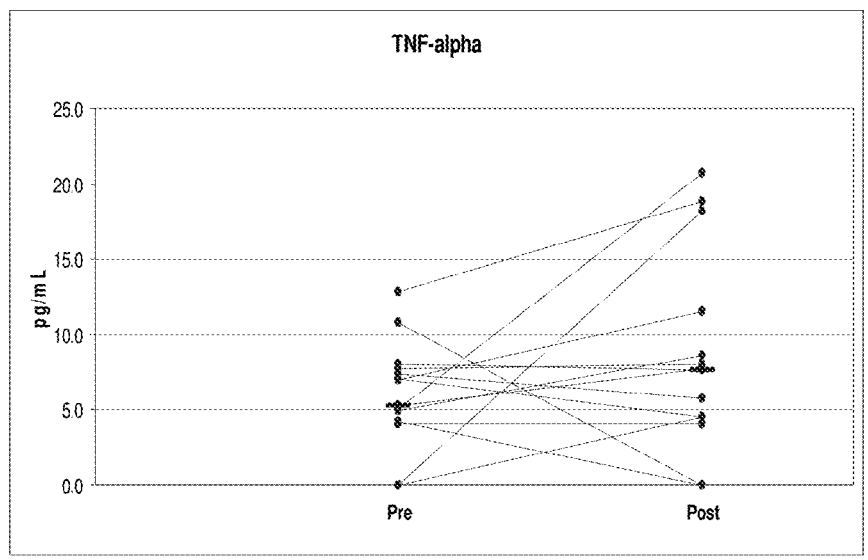
FIG. 9 is a graph illustrating individual sputum TNF-α level before and after study drug inhalation. Slash marks represent the median level.
Figure 10:
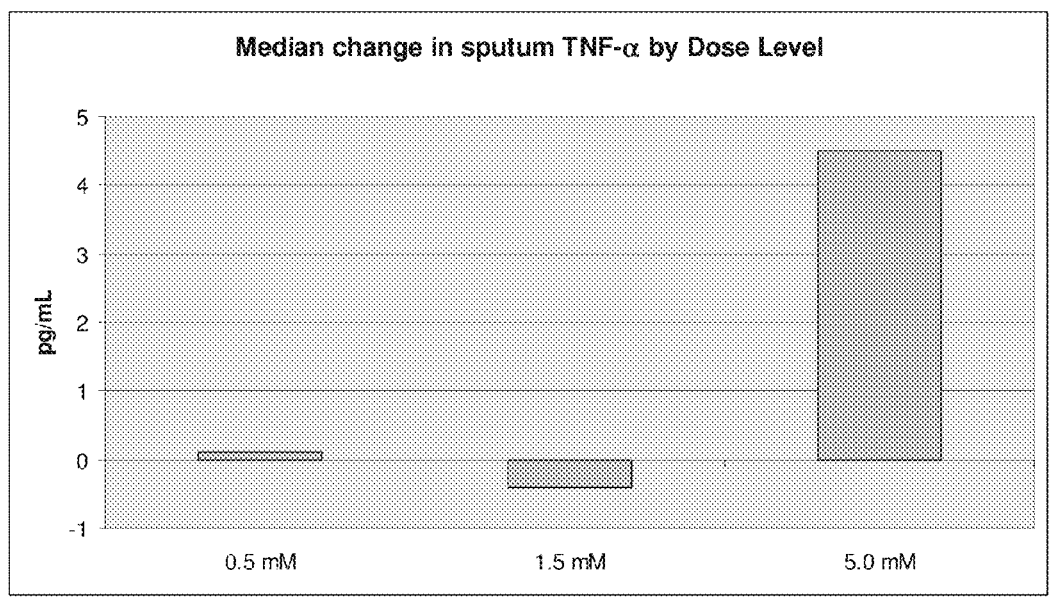
FIG. 10 is a graph illustrating median change from pre- to post-study drug inhalation in sputum TNF-α levels and by drug dose level.

As set forth above, FIG. 1 is a graph illustrating individual sputum total protein levels before and after study drug inhalation. Slash marks represent the median level. FIG. 2 is a graph illustrating median change from pre- to post-study drug inhalation in sputum total protein levels and by drug dose level while FIG. 3 is a graph illustrating individual sputum free elastase levels before and after study drug inhalation. FIG. 4 is a graph illustrating median change from pre- to post-study drug inhalation in sputum free elastase levels and by drug dose level. FIG. 5 is a graph illustrating individual sputum IL-6 levels before and after study drug inhalation. FIG. 6 is a graph illustrating median change from pre- to post-study drug inhalation in sputum IL-6 levels and by drug dose level. FIG. 7 is a graph illustrating individual sputum IL-8 levels before and after study drug inhalation. Slash marks represent the median level. FIG. 8 is a graph illustrating median change from pre- to post-study drug inhalation in sputum IL-8 levels and by drug dose level. FIG. 9 is a graph illustrating individual sputum TNF-α levels before and after study drug inhalation. FIG. 10 is a graph illustrating median change from pre- to post-study drug inhalation in sputum TNF-α levels and by drug dose level.

Given the changes noted in the cell counts (both in peripheral blood and sputum) this finding is intriguing. Since evidence for cellular influx was noted, it would have been expected to see this paralleled by a corresponding increase in cytokines and particularly in the free elastase activity. The study drug blocked this pro-inflammatory effect.

The data clearly showed that pyruvate can up or down regulate inflammation depending on concentration. White blood cell counts were reduced 25% with the inhalation of 5 ml of 0.5 mM sodium pyruvate, as was total proteins, elastase, as were IL-6, IL-8, and TNF-α. White blood cell counts were increased by 25% with the inhalation of 5 ml of 5 mM pyruvate or higher as was the total proteins, elastase, IL-6, IL-8, and TNF-α.

Tissue Culture Studies

To investigate the ability of pyruvate to regulate the inflammatory process during an infection, the MatTek Epi-Derm Assay was used. The MatTek Epiderm tissue samples were treated with pyruvate and the combination of pyruvate and α-ketoisovalerate both at 20 mM concentrations or higher to determine if the combination would regulate IL-I and IL-8 up or down during a simulated infection. Following a one-hour equilibration, the Epiderm tissues were placed into the incubator (37° C., 5% $CO_2$) in assay medium. The old medium was replaced with fresh medium and the test articles were applied to the tissue samples. The test articles remained in contact with the tissue for various dosing times, one hour, then at four hours, and at 20 hours. The testing was run in duplicate. Various immunostimulators sodium dodecyl sulfate (SDS), glycoprotein D (gpD) were used singly or with the α-keto acids to replicate an infection, along with vehicle controls. Untreated samples were used as negative controls. Following treatment, the media from the tissues samples were tested in Elisa kits for IL-1 and IL-8 according to the manufacture's protocols.

The 0.5 mM levels of sodium pyruvate using 5 ml samples contain 0.28 mg of sodium pyruvate. The 10 mM levels of sodium pyruvate using 5 ml contain 5.6 mg of sodium pyruvate. The 20 mM levels of sodium pyruvate using 5 ml contain 11.2 mg of sodium pyruvate. The 40 mM levels of sodium pyruvate using 5 ml contain 22.4 mg of sodium pyruvate.

A quantity of 5 ml of 0.1 mM to 100 mM of α-keto isovalerate was used. A quantity of 5 ml of 20 mM of α-keto isovalerate contains 13.8 mg. A quantity of 5 ml of 40 mM of α-keto isovalerate contains 27.6 mg. A quantity of 5 ml of 100 mM of α-keto isovalerate contains 69 mg.

Results

The primary end points were the levels of IL-8 and IL-1 after treatment with an immunostimulator, pyruvate and the combination of pyruvate and α-ketoisovalerate. The immunostimulator did not increase the cytokines by themselves. This model did not have white blood cells to respond to the immunostimulator or produce oxygen radicals. The α-keto acids did not increase the cytokines also in this model. The immunostimulators in combination with pyruvate and α-ketoisovalerate increased IL-8 over 300%, which shows direct antimicrobial activity, compared to the untreated controls. IL-8 activates neutrophils to increase their numbers at the infected site. In the same experiment, IL-1 was decreased significantly (over 200%). IL-1 increases inflammation and decreases healing times. This test clearly showed that the α-keto acids regulated the inflammatory process in dermal tissues in a manner that would increase the bodies ability to fight infected wounds and increase the body's ability to healing quicker. The same experiment was done with virally infected cells and the pyruvate and combination of pyruvate and α-ketoisovalerate decreased viral plaque formation by 50%. Viral plaques are a direct measure of viral numbers in infected cells. The antiviral drug, Acyclovir also decreased viral plaques by 60% and the α-keto acids in combination with acyclovir, totally eliminated the virus from the infected cells.

Example 2

Inhaled Sodium Pyruvate for the Treatment of Cystic Fibrosis and other Lung Diseases Cystic fibrosis (CF) is the most common, lethal inherited disease of Caucasians. Approximately 30,000 people in the United States and 70,000 worldwide have a diagnosis of CF. It is caused by mutations in the cystic fibrosis transmembrane regulator (CFTR) gene. The clinical manifestations characteristic of CF include progressive bronchiectatic lung disease with thick mucus production and colonization by *Pseudomonas aeruginosa*. The CFTR gene mutation results in altered cell transport properties, which affect both chloride and glutathione secretion. Chronic inflammation, associated with activated neutrophils and macrophages, is a common feature of CF. Highly reactive toxic oxygen (superoxide anion, free hydroxyl radical, hydrogen peroxide) and nitrogen species (NO, peroxynitrites) are abundant in the chronic inflammatory response in CF and appear to playa prominent role in the pathogenesis of this disease as are excess levels of inflammatory cytokines.

A total of fifteen 15 CF and 10 Asthmatic/COPD patients were treated with varying doses of sodium pyruvate. The therapeutic dose, 0.5 mM of sodium pyruvate lowered the inflammatory cytokines (markers) including, IL-6, IL-8 by 200% or more. IL-10 was not affected. The 5.5 mM or higher concentrations of sodium pyruvate increased only IL-8. The 10 mM solution of sodium pyruvate produced the best results by increasing the inflammatory cytokines IL-8 and IL-10 by 200% or more which was a surprise. The 0.5 mm can be used in CF patients to lower inflammation and white blood cell numbers and the 5.5 mM or higher can be used to increase cytokines and white blood cell numbers needed to fight infections and balance the immune system, especially if the patient is using inhaled steroids.

Treatment of HSV-I infected cell with various α-Keto Acids
α-Keto acids regulation of inflammatory anti viral cytokines at varying mM concentrations α-Keto Acids tested Alone for their Ability to Reduce Viral Plaques (numbers live viruses)
Percentage of viral plaque reduction in virally infected cells

|  | pyruvate | α-keto isovalerate | α-keto butyrate | pyruvate + α-keto isovalerate | pyruvate + α-keto butyrate |
|---|---|---|---|---|---|
| 05 mM | 5% | 0% | 0% | 10% | 0% |
| 10 mM | 10% | 5% | 0% | 20% | 3% |

-continued

Treatment of HSV-I infected cell with various α-Keto Acids
α-Keto acids regulation of inflammatory anti viral cytokines at varying mM concentrations

| 20 mM | 38% | 10% | 0% | 50% | 30% |
| 40 mM | 50% | 20% | 5% | 74% | 40% |

α-Keto Acids in Combination with Acyclovir (therapeutic dose)
Percentage of viral plaque reduction in virally infected cells (reduction of live viruses)

|  | Pyruvate Acyclovir | α-keto isovalerate Acyclovir | α-keto butyrate Acyclovir | therapeutic dose Acyclovir alone |
| --- | --- | --- | --- | --- |
| 10 mM | 66% | 42% | 39% | 40% |
| 20 mM | 90% | 55% | 40% |  |

α-Keto Acids Combinations with Acyclovir
Percentage of Viral Plaque Reduction in Virally Infected Cells

|  | Pyruvate α-keto isovalerate Acyclovir | pyruvate α-keto butyrate Acyclovir |
| --- | --- | --- |
| 10 mM | 78% | 63% |
| 20 mM | 100% | 70% |

The results clearly show that pyruvate was the only α-keto acid that increased the inflammatory cytokines high enough needed to kill high numbers of the virus in virally infected cells as measured by reduction in viral plaques. Acyclovir a known anti-viral agent, also reduced viral plaques. Unexpectedly, the combination of pyruvate and α-keto isovalerate produced the best results, by totally eliminating the virus from the infected cells. Inhalation of pyruvate at 0.5 mM reduced the levels of white blood cells, elastase, IL-8, IL-6 and did not increase levels of TNF-α. Inhalation of more than 5 mM of pyruvate in humans increased levels of white blood cells elastase, IL-8, IL-6, IL-10 and TNF-α (cytokines) that would be used to kill viruses in the lungs. This tissue culture data along with data from humans, confirms that some α-keto acids worked and some like α-keto butyrate did not. It appears that α-keto butyrate will reduce inflammation and the production of cytokines, even during an infection.

Example 3

Nicotine/Pyruvate Inhalation Delivery to the Sinuses or Lungs

Nicotine was formulated as a modified sodium pyruvate 20 mM nasal solution which was then administered as an inhaled mist to the lungs or nasal cavity. A number of clinical test patients squirted each nostril three times each, 2 times per day which amounted to 2.94 mg-4.2 mg of pyruvate and approximately 0.020 mg to 0.5 mg of nicotine per daily dose. A patient that used Nicotrol (nicotine nasal spray) for smoking cessation was treated with a nasal spray of sodium pyruvate 20 mM to 40 mM prior to using his nasal inhaler. Each metered dose of Nicotrol delivers 0.5 mg of nicotine. The administration of the 20 mM spray of nicotine/sodium pyruvate solution allowed the patient to control his nicotine addiction using less medication and eliminated the irritation and nose soreness associated with nasal nicotine formulations such as Nicotrol. Nicotine inhalation can increase the risks of nasal and lung infections and nicotine can suppress certain components of the immune system. The 20 mM pyruvate solution in combination with nicotine reduced the negative effect of nicotine and enhanced the effect of nicotine as a stimulant. High levels of pyruvate, 5.5 mM to 40 mM or higher up-regulate the immune system and its inflammatory agents to balance out the negative suppressive effects of inhaled nicotine. It was found that the inhaled nicotine/pyruvate solution, delivered nasal or directly to the lungs, was well tolerated over nicotine by itself, which was irritating. The combination also proved to be synergistic in the observed effects. On a scale of 1-10 with 10 being very irritating and 1 being non-irritating, nicotine solutions delivered without pyruvate were rated a score of 8.0 by 6 patients and those nicotine solutions with pyruvate were rated a 2.0 by the same patients, a 60% reduction in irritation. Smokers who used this formula rated the pyruvate/nicotine formula more efficacious in the ability to control their smoking and since it was much less irritating and "patient-friendly", it was rated as being much more effective than nicotine alone.

Example 4

Insulin/Pyruvate Inhalation in the Sinuses or Lungs

Insulin is an animal hormone, produced in the pancreas, whose presence indicates to the body and the body's cells that the animal is well fed, causing liver and muscle cells to take in glucose and store it in the form of glycogen, and fat cells to take in blood lipids and turn them into triglycerides. Insulin is used to treat some forms of diabetes mellitus. Patients with type-1 diabetes mellitus depend on external insulin (most commonly injected subcutaneously) for their survival because of the absence of the hormone. Patients with type-2 diabetes mellitus have insulin resistance, relatively low insulin production, or both; some type 2 diabetics eventually require insulin when other medications become insufficient in controlling blood glucose levels. Chemically, insulin is a peptide hormone comprised of 51 amino acid residues and its' structure varies marginally between species of animal. Bovine insulin differs from human in only three amino acid residues, and porcine insulin in one. Even insulin from some species of fish is similar enough to human to be effective in humans. The C-peptide of proinsulin, however, is very divergent from species to species. All structures of insulin useful in humans, including synthetic "human" insulin, may be employed in the present invention however, insulin cannot be taken orally. When prescribed, every individual's dose must be adjusted for that individual's particular situation. There are several ways to dose short-acting as well as rapid-acting insulin. The following table outlines estimates of the recommended starting inhaled insulin dosages (based on body weight).

| Weight | Starting Inhaled Insulin Dose | Blisters |
| --- | --- | --- |
| 66 to 87 pounds | 1 mg per meal | One 1-mg blister |
| 88 to 132 pounds | 2 mg per meal | Two 1-mg blisters |
| 133 to 176 pounds | 3 mg per meal | One 3-mg blister |
| 177 to 220 pounds | 4 mg per meal | One 1-mg blister plus one 3-mg blister |
| 221 to 264 pounds | 5 mg per meal | Two 1-mg blisters plus one 3-mg blister |
| 265 to 308 pounds | 6 mg per meal | Two 3-mg blisters |

It was surprisingly discovered that inhaling insulin with pyruvate reduced the irritation produced from insulin and produced better results than the use of insulin by itself. Diabetics that inhale insulin have difficulty if they have a pulmonary disease like COPD, which effects the dosage received. The addition of pyruvate enhanced insulin uptake for patients that have diabetes with pulmonary lung or sinus diseases. The inhalation of insulin cannot only be used to treat diabetics, but can be used to treat Alzheimer's disease as well. In one patient with diabetes and mild Alzheimer's the inhalation of insulin with pyruvate improved mental functions over the same concentration of inhaled insulin alone. It was discovered that inhaled pyruvate may increase IL-10 production in the brain thus increasing the efficacy of inhaled insulin, thereby increasing the cognitive functions in Alzheimer's patients. It has also been shown that certain immune system components when increased, enhances cognitive functions and decreased the amyloid protein, known to disrupt cognitive functions.

Preliminary Cognitive Testing: Three-word Recall, "Mini-cog" and Coin Counting

The following two tests can help gauge memory function when patients express concern. The tests also may help identify patients who need more thorough evaluation. All of these tests are relatively free of influence by educational level:

1. A Three-word Delayed Recall Exercise
   - The patient is told to remember three words, these being three common nouns, such as horse, pencil and rose. The patient was then asked to repeat them.
   - About five minutes later, the patient was then asked recall them.
   - Individuals without impairment should be able to remember all three words, especially with such prompts as, "The first word was the name of an animal,"
   - Remembering only one or two words indicates a need for further evaluation.
2. The "Mini-cog" Test, Combining Three-word Recall with Clock-drawing
   - Three simple nouns were given and the patient was asked to repeat them,
   - The patient was then asked to draw the face of a clock on a sheet of paper, showing the time as 10 minutes past 11.
   - After the clock has been drawn, ask the patient to repeat the three words.
     - Patients who remember all three words have no dementia.
     - Patients who remember none of the words should receive further evaluation,
     - if the patient remembers one or two words, the physician should refer to the score on the clock drawing to help interpret this
       - normal clock=non-demented
       - abnormal clock=further evaluation needed
     - Patients who recall all three words but have a problem with the clock may also require further evaluation.
   - More about clock-drawing and scoring
     - When stating the time to be shown on the clock, avoid referring to the "hands" of the clock to avoid prompting. Rather, say "Show the time as 10 past 11."
       - "10 past 11" tests the ability to translate "10 past" into the right numerical value.
       - It also requires the use of both halves of the clock face.
     - There are several scoring systems. A simple one is based on four points, with a lower score suggesting further evaluation.
       - One point is given for drawing a closed circle. Some clinicians prefer to give patients a pre-drawn circle, so that any accidental distortions in shape do not affect the placement of the numbers.
       - One point is awarded for including the 12 correct numbers.
       - One point is given for putting the numbers in the correct position.
       - One point is awarded for drawing the hands to show the correct time.

Using the above described tests, on this diabetic Alzheimer's patient, the inhalation of insulin by itself improved cognitive function moderately, over base scores, with the patient being able to increase his scores by 40% over the non use of insulin. When pyruvate was administered by itself his scores increased by 45% over base measurements. The combination of insulin and pyruvate increased his cognitive abilities to nearly 90%, showing that pyruvate and insulin are synergistic.

In the present example, insulin was administered to the lungs of each patient in a 5 mL 20 mM pyruvate solution. For the nasal cavity, each nostril of the patient was squirted three times each, 2 times per day which comprises 2.94 mg of pyruvate. Insulin inhalation can increase the risks of nasal and lung infections and insulin can suppress certain components of the immune system. The 20 mM pyruvate solution in combination with insulin balanced the negative effect of insulin and enhanced the effect of insulin. High levels of pyruvate, 5.5 mM to 40 mM or higher up-regulate certain components of the immune system and its inflammatory agents to balance out the negative suppressive effects of inhaled insulin and to enhance its uptake. Many investigators have shown that inhaled insulin can suppress the immune system, thus the use of high levels of pyruvate was shown to up-regulate key components of the immune system and reduce the inhibitory effects of insulin on the production of key inflammatory agents. In subsequent experiments, high levels of inhaled pyruvate over 5 mM (10-20 mM) has been shown to increase IL-10 in both the sinuses and lungs.

Example 5

Thirty-nine (39) subjects who were regular nasal spray users due to chronic sinusitis or allergic rhinitis and other sinus diseases were recruited for a one week open label, in home-use trial. Allergic rhinitis and other sinus diseases result in the elevation of certain inflammatory components and the concurrent down regulation of some other inflammatory components. When this happens, infections can occur. The ability to up-regulate these immune components helps balance the nasal immune system to inhibit infections and minimize injury to surrounding tissues. Six (6) different sodium pyruvate+saline combination nasal sprays, based on concentrations of saline and sodium pyruvate, were administered to the subjects, and each of the test products were used by at least six subjects. The subjects used the test nasal sprays at home (two to three sprays; two or three times a day) for seven days, in place of their regular nasal spray.

Prior to, and at the end of the study period, the subjects' nostrils were examined for mucosal fragility, lesions, erythema, and edema using a rhinoscope.

Thirty-eight subjects completed the study. The data obtained from the rhinoscopic examinations indicated that none of the six (6) sodium pyruvate+saline nasal spray test products induced nasal fragility, lesions, erythema, or edema. The test formula ranged from 0.5 mM solutions to 20 mM solutions. A 40 mM sodium pyruvate solution was tested and this was also favorably rated by the patients. The 0.5 mM to 5 mM pyruvate solutions were rated non-effective to less effective by the patients when compared to the 20-40 mM pyruvate solutions. In this case we delivered the 20 mM solution nasal solution with sodium pyruvate. The patient squirted each nostril three times each, 2-3 times per day is 2.94 mg to 3.8 mg of pyruvate delivered per daily dose. All the test sprays were preserved with 0.02% benzalkonium chloride.

81% of all subjects said the 0.45% sodium chloride/sodium pyruvate 20 mM (5 ml contains 11 mg of pyruvate) was "Better Than" or "Comparable" to their present therapy with regard to less "Stinging." When questioned by the Investigator, 35 of 39 (90%) subjects stated that the Pyruvate+Saline Nasal Sprays "Opened Nasal Passages," and "Cleared/Reduced Congestion." This product received an overall rating of 8.0, with all characteristic evaluations rated between 7.6 and 8.7 ("Likely to Buy"). A nasal wash delivered 10 mls of the 20 mM pyruvate solution which is 22 mg of pyruvate being delivered.

This study clearly showed that delivery of high levels of sodium pyruvate can reduce the toxic effects of inhaled pollutants, nasal sensitivity, soreness, mucus congestion, swelling, and enhanced the patients' ability to sleep. The formulations were soothing to the nostrils, relieving nasal symptoms, of congestion, irritation, redness, snoring.

Example 6

Eighteen subjects who were regular nasal spray users were given EmphyClear™, a sodium pyruvate/saline nasal spray to use at home two or three times a day for seven days, in place of their regular nasal spray. Several of these subjects regularly used saline, or OTC nasal products, including antihistimines and several used steroid-based nasal sprays. These patients suffered from nasal diseases caused by dusts, allergies and pollutants from irritant gases which cause allergic rhinitis, sinusitis, and other nasal diseases. Prior to, and at the end of the study period, the subjects' nostrils were examined for mucosal sensitivity, fragility, lesions, erythema, and edema using a rhinoscope. These pre- and post-study nasal characteristics were rated on a five point scale, zero ("none") to four ("severe") scale, and compared.

All 18 subjects completed the study, and none opted to return to their normal nasal spray therapy during this period. The data obtained from the rhinoscopic examinations indicated that the sodium pyruvate/saline nasal spray did not induce dermal irritation and was effective in significantly ($p=0.006$) reducing the erythema in subjects who normally use either saline or non-saline nasal sprays including steroids when pre-test ratings were compared to post-test ratings. Further, subjective evaluations from the subjects indicated a positive preference for the sodium pyruvate/saline nasal spray, with 83% of all subjects saying EmphyClear™ was "Better Than" or "Comparable To" their present therapy with regard to "Soothing;" and a like percentage of all subjects saying EmphyClear™ was "Better Than" their present therapy for relieving symptoms.

Ninety-four percent (94%) of all subjects said it was "Better Than" their present therapy with regard to less "Stinging." When questioned by the Investigator, 17 of 18 subjects stated that EmphyClear™ "Opened Nasal Passages," and "Cleared Congestion and reduced snoring, moisturized their nasal passages and enhanced their ability to sleep all night." These results were consistent whether the subject normally used a saline or steroid-based nasal spray. This study clearly showed that delivery of high levels of sodium pyruvate can reduce the toxic effects of inhaled pollutants, nasal fragility, congestion do to mucus, swelling, and enhanced their sleeping. Five of these patients suffered continuously form various forms of sinusitis, (viral or bacterial infections) and while using the pyruvate solutions reported that their sinusitis decreased or disappeared.

Example 7

A consumer at-home trial comprising a three-month evaluation study was conducted in which thirty-one (31) subjects that normally used nasal sprays were asked to evaluate the three different sodium pyruvate solution concentrations over a period of three months. The sodium pyruvate+saline nasal sprays contained 0.45% saline+either 5 mM, 10 mM or 20 mM sodium pyruvate. The subjects were asked to evaluate the three products in terms of congestive relief, and to indicate any preferences between the three concentrations of sodium pyruvate.

The 0.45% saline+20 mM Sodium Pyruvate nasal spray was the preferred product with an overall rating of 90%. 29 out of the 31 subjects (94%) stated that this product ". . . opened their nasal passages and cleared their congestion and allowed them to sleep longer and sounder."

In all, 88 patients suffering with allergic rhinitis, sinusitis, other sinus diseases, or were smokers, or had various lung diseases, including COPD, ILD, with one patient with an HIV infection, were tested with various different Sodium Pyruvate formulae (5.5 mM to 40 mM) and 81 patients (92%) stated that the Pyruvate+Saline Nasal Sprays opened their nasal passages and cleared their congestion for over 12 hours and enhanced sleep Five of these patients suffered continuously from various forms of sinusitis, (viral or bacterial infections) and while using the pyruvate solutions reported that their sinusitis decreased or disappeared. In each study the sodium pyruvate+saline nasal sprays were objectively and subjectively judged to be "Comparable To" or "Better Than" Saline or Steroid-based commercial nasal sprays. High levels of inhaled pyruvate selectively up-regulated certain inflammatory agents to fight infections, and to balance out the negative effects of inflammation. In normal patients that had no lung or sinus disease or inflammation, high levels of inhaled pyruvate produced no effect beyond soothing the sinuses and relieving snoring. As discussed infra at page 2, when some inflammatory agent levels are elevated, others are suppressed and abnormally low due to disease or inflammation. For example, in allergic rhinitis, IL-10 is suppressed, as are some of the other cytokines.

On the other hand, inhaling high doses of pyruvate enhances and balances the immune system. This reduces tissue and cellular damage, and reduces or eliminates infections. IL-10 is capable of inhibiting synthesis of pro-inflammatory cytokines and also displays a potent ability to suppress the antigen-induced reactions, thus up-regulating IL-10 has been shown to be effective in treating allergic rhinitis. Testing the lungs or sinuses of several patients for increases in cytokines, as outlined in example 1, demonstrated that IL-10 increased by 380% with the inhalation of a 20 mM pyruvate solution. The increase in IL-10 levels reduced nasal congestion and fragility, irritation and reduced the allergic reaction to dust, pollen, mold, and other allergens. This also resulted in a reduction in snoring that was subsequently reported by most patients.

Example 8

Nine regular Flonase® subjects and eight regular Nasacort® subjects who suffered chronically from allergic rhinitis and sinusitis from dust, allergens, gases, mold, and pollen, were recruited to evaluate comparable products containing a reduced level of steroids (50-70% reduction in the drug) in a sodium pyruvate nasal solution. Prior to beginning the study, the subjects were asked to rate their current product on a 10 point visual analogue scale (VAS) with a value of 0 being "terrible" and 10 being "excellent" for the following categories: a) soothing the nostrils; b) relieving sinus symptoms; c) stinging of the nostrils, and overall rating of satisfaction. The subjects on average rated their current products "good," with little difference between the two products except for a trend toward perceived better "soothing" with Nasacort® than with Flonase®.

At the start of the trial, the subjects were blinded regarding their test product, and the test product was used exclusively for 14 days. The subjects' nostrils were then objectively evaluated using a nasoscope at days 0, 7, and 14, and physical exams, including vital signs were also administered at this time. During the 14 day test period, the subjects subjectively evaluated the test product on a daily basis using a 10-point VAS questionnaire. The categories included comparison of the test products to the subjects' normal therapy in their ability to sooth the nostrils, relieve symptoms, cause/reduce stinging, relieve congestion, and quantify usage, and rate the product on an "overall" basis.

After seven and fourteen days, nasoscope evaluations revealed a trend in reduction of aberrant morphologies for the "Reduced-Strength Flonase®" Test product compared to the nasoscope evaluations obtained on Day 0; and a significant reduction in aberrant morphologies for the "Reduced-Strength Nasacort®" Test product. These objective observations are consistent with the subjective evaluations where the subjects rated the "Reduced-Strength Flonase®" product as "Comparable" or "Better" in all categories, and rated "Reduced-Strength Nasacort®" Test product as "Better" in all categories.

The test products were subjectively judged to be comparable or better than the Flonase® or Nasacort® that the subjects typically used. The subjects did not rate the test products lower than the Flonase® or Nasacort® in any category. The test products were rated as "Better" in comparison to the "Soothing," "Stinging" and "Relief of Symptoms" characteristics of Flonase®, and, with regard to Nasacort®, the subjects rated the Test product as "Comparable" across all categories after 14 days of use. End-of-Trial subjective comments were also highly favorable to the Test products compared to Flonase® and Nasacort®. Additionally, when asked if they might purchase the product, the subjects' average result was 5.4±1.0, indicating that the subjects "Might Purchase," or were "Likely to Purchase," the Test product.

An analysis of the results conclusively showed that the "Reduced-Strength Flonase®" and "Reduced-Strength Nasacort®" Test product nasal sprays were found to be as effective as the "full-strength" (i.e. commercial) Flonase® and more effective than the commercial Nasacort® when the reduced commercial "active ingredients" were delivered to the subjects in a sodium pyruvate solution.

The sodium pyruvate and steroids in the nasal spray were found to act synergistically. By themselves, steroids will shut down the immune system and thus can be toxic, irritating, and habit forming which thereby increases the percentage of infections in patients. When formulated in solution with pyruvate, the steroids were found to act synergistically which enabled the reduction of inhaled steroid levels and complemented their reactions in the human body. Inhaled corticosteroids reduces macrophage inflammatory protein-1-α-granulocyte-macrophage colony-stimulating factor, cytokines and interferon-gamma release from alveolar macrophages in asthma, which increases infections. Asthma is characterized by a reduced capacity to produce IL-10.

The 0.5 mM pyruvate/steroid solution that was used to reduce inflammation and inflammatory markers in the lungs, did not up-regulate inflammatory markers in the nasal cavities or lungs, whereas the 5.5 mM (2.9 mg) to 20 mM sodium piruvate/steroid solution did. This was unexpected. The 5.5 mM to 20 mM pyruvate solutions in combination with reduced steroids balanced their negative effect and enhanced their efficacy that allowed for the formulation of an efficacious nasal spray with a reduction of the steroids by 70%. Steroids suppress the immune system to the point that patients that use steroids have a very high rate of infection. High levels of pyruvate, i.e. 5.5 mM to 40 mM or higher, up-regulate the immune system and its inflammatory agents and this balances the negative immune suppressive side effects of steroids. During allergic rhinitis or other sinus diseases, certain inflammatory components are elevated, whereas certain other inflammatory components are down regulated, and in the process infections can occur. The ability to up-regulate these immune components help balance the nasal and lung immune system to inhibit infections and minimize injury to surrounding tissues and reduce steroids by 70%. In Allergic Rhinitis, IL-10 is suppressed, as are some of the other cytokines.

Allergic reactions include four types of reactions, i.e., types I, II, Ill and IV. The type I (immediate-type, anaphylactic) allergic reaction is triggered by the reaction-relating-factor immunoglobulin E (hereinafter abbreviated as an IgE antibody). The reaction steps can be divided roughly into the following three steps. The first step is a sensitization step involving IgE antibody production and binding of the resulting IgE antibodies to mast cells or basophiles. The second step involves degranulation of the mast cells or basophiles and release of chemical mediators. The third steps involves onset of effects of the released chemical mediators on the target organs. Thus, the type I allergic reaction against foreign antigens leads to onset of symptoms through the above reaction steps. Only symptomatic treatments by inhibiting the above second and/or third reaction steps have been carried out to treat allergic diseases. That is, the treatments are carried out by inhibiting the release of chemical mediators accompanying the degranulation and/or by inhibiting allergic reactions induced by the released chemical mediators. These symptomatic treatments have been known to be effective not only in systemic administration of anti-allergic agents but also in their topical administration to the nose, etc. However, the effects of the treatments are limited because the treatments do not inhibit IgE antibody production which is the basic first step of the type I allergic reaction.

However, because the mechanisms of nasal topical IgE antibody production are not clear, there is no report on effects of nasally topically administered drugs applicable to nasal topical membrane allergic reaction. As described above, there is no satisfactory anti-allergic pharmaceutical compositions that are effective and safe in nasal topical administration until now. In doing nasal lavage studies, up-regulating certain cytokines, like IL-10, by using high levels of pyruvate has been shown to inhibit IgE antibody production.

The data and clinical results clearly show that patients who use a steroid/pyruvate nasal formulation will reduce their chances of infections and tissue damage. In a similar experiment described above, a commercial Rhinocort® nasal formula (32 mg of budesonide) was diluted with saline to deliver 16 mg of budesonide (50% of the commercial formulation) to the 4 patients that use Rhinocort and that suffered with allergic rhinitis and sinusitis, and other nasal inflammatory diseases. These patients rated budesonide a score of 8.0 on a 1-10 irritation scale with 1 being perceived as non-irritating and 10 being perceived as very irritating to the sinuses. These patients dosed each nostril 2-3 times, four to six times daily to achieve efficacy of their current product, which is 24-36 daily squirts, far exceeding the recommended FDA standards of 240 mg daily amount. When these patients tested the 50% formulation with the 5.1 mM sodium pyruvate solution, they obtained the same efficacy, but with half the needed amount of the steroid, but still used 18-24 squirts daily, which exceeds the FDAs' recommended daily limits. They rated the product a 5. When these patients tested the 50% steroid formula with the 20 mM sodium pyruvate, they rated the product a 2 and all the patients recorded a 20%-30% reduction in usage, 8-12 squirts daily usage, clearly showing that the 20 mM pyruvate formulation was synergistic and un expectedly less irritating to the nasal cavities and sinuses and did not exceed the FDA limits of daily steroid usage. A 20 mM solution nasal solution of sodium pyruvate squirted into each nostril three times each 2-3 times per day is 2.94 mg to 3.65 mg of pyruvate delivered per daily dose.

Ribavirin Inhaled Antiviral and Mupericin Inhaled Antibacterial

This medication is an anti-viral drug used to treat infants and young children who have a severe lung infection caused by a certain virus (respiratory syncytial virus-RSV). Nearly all children become infected with this virus before they are 3 years old. Most cases are mild and do not require anti-viral drugs. This medication is used to treat severe RSV infections that need treatment in a hospital. This medication is given by continuous inhalation, usually for 12 to 18 hours daily for 3 to 7 days or as directed by the doctor. A special machine (small-particle aerosol generator) is used to make a mist, which is then inhaled through the mouth or nose. Chest soreness may occur. Redness/irritation of the nasal cavities and eye or eyelid may also occur. When five (5) mls. of a 10 mM solution of pyruvate was used prior to the administration of this medication; the patient reported that the irritation and chest soreness was eliminated. High levels of pyruvate 5.5 mM or higher have been shown to up-regulate certain components of the immune system to kill virally infected cells. Tissue culture studies with HSV-1, HSV-2 and various rhinoviruses, have shown that 10-40 mM concentrations of pyruvate reduced viral plaques by 40-60% by increasing the synthesis of various cytokines. The combination of various antivirals with pyruvate totally eliminated the virus infection in cells. The inhalation of 5.0 mls of a 20 mM solution of sodium pyruvate used by itself reduced viral infections in a patient with sinusitis by 50%. When Mupericin, an antibacterial agent, was formulated in a nasal wash comprising in the 20 mM sodium pyruvate solution and administered to two (2) patients that suffered from bacterial infections 10 or more times annually, the amount of bacterial infections was reduced dramatically.

REFERENCES

1. Hardman, J. et al., The pharmacological basis of therapeutics. Ninth edition 1996, pp. 137-356.
2. Moncada, S. et al, Nitric Oxide: physiology, pathophysiology, and pharmacology. 1991 Pharmacological Reviews Vol. 43 no pp 109-141.
3. Nathan, C., Nitric oxide as a secretory product of mammalian cells. FASEB Journal vol. Sep. 6, 1992 pp 3051-3064.
4. Rossaint, R. et al, Inhaled nitric oxide: its effect on pulmonary circulation and airway smooth muscle cells. Euro Heart Jour. 1993 vol. 14 Supp. pp 133-140.
5. Mattes, K. et al. NO in exhaled air is correlated with markers of eosinophilic airway inflammation in corticosteroid-dependent childhood asthma. Euro Respir J. 1999 vol. 13, pp 1391-1395
6. Artlich, A. et al., Childhood asthma: exhaled nitric oxide in relation to clinical symptoms. Euro Respir. J. Vol. 13, pp 1395-1401.
7. Jobsis, Q. et al. Sampling of exhaled nitric oxide in children: end expiratory plateau, balloon and tidal breathing methods compared. Euro Respir. J. Vol. 13, pp 1406-1410.
8. Mukala, K. et al. Personally measured weekly exposure to $NO_2$ and respiratory health among preschool children. Euro. Respir. J. Vol. 13, pp 1411-1417.
9. Stanko R., The power of Pyruvate 1999, Keats Publishing.
10. Kelly, F. et al. Antioxidant kinetics in lung ravage fluid following exposure of humans to nitrogen dioxide. Am. J. Respir. Crit Med. Vol. 154 1991 pp 1700-1705.
11. Roberts, J. et al. Inhaled nitric oxide and persistent pulmonary hypertension of the new borns. The new England Journal of Medicine Feb. 27, 1997 pp 605-610.
12. Lehninger 1981 Biochemistry, Worths Publishing.
13. Comhair, S. et al. Rapid loss of superoxide dismutase activity during antigen-induced asthmatic response. Lancet vol. 355 February 192000.
14. Stewart R M, et al., Hydrogen peroxide contracts airway smooth muscle: a possible endogenous mechanism. Respir. Physiol 1981 45: 333-342.
15. Rhoden K J, Barnes P J: Effect of hydrogen peroxide on guinea pig tracheal smooth muscle in vitro: role of cyclo-oxygenase and airway epithelium. Br. J Pharmacol 1989 98: 325-330
16. Motojima S, et al. Toxicity of eosinophil cationic proteins for guinea pig tracheal epithelium in vitro. Am Rev Respir Dis 1989 139: 801-805
17. Sporn P H, et al. Hydrogen peroxide induced arachidonic acid metabolism in rat alveolar macrophage. Am Rev Respir Dis 1988 137: 49-56
18. Postma, D. S. et al Association between nonspecific bronchial hyperreactivity and superoxide anion production by polymorphonuclear leukocytes in chronic air flow obstruction. Am. Rev Respirdis. (1988) 137: 57-61.
19. Alving, K. Methodological aspects of exhaled nitric oxide measurements Euro Respir Rev 1999: 9:68, 208-211
20. Kharitonov, S. Exhaled nitric oxide and carbon monoxide in asthma. Euro Respir. Rev. 1999, 9:68, 212-216.
21. Gouw, P. et al. Stimuli affecting exhaled nitric oxide in asthma. Euro Respir. Rev. 1999; 9:68, 219-222.
22. Kharitonov, S. Exhaled nitric oxide and carbon monoxide in respiratory diseases. Euro Respir. Rev. 1999; 9:68, 223-226.
23. Barnes, P. The effect of drugs on exhaled nitric oxide. Euro Respir. Rev. 1999; 9:68, 231-233.
24. Baraldi, E. et al. Application of exhaled nitric oxide measurement in pediatrics. Euro Respir. Rev. 1999; 9:68, 234-240.
25. Lundberg, J. Nitric oxide in the nasal airways. Euro Respir. Rev. 1999; 9:68, 241-245
26. Culpitt, S. The measurement of hydrogen peroxide in airways disease. Euro Respir. Rev. 1999; 9:68, 246-248.

27. Montuschi, P. Isoprostanes and other exhaled markers in respiratory diseases. Euro Respir. Rev. 1999; 9:68, 249-253.
28. Robertson, F M, Gene expression and cellular sources of inducible nitric oxide synthase during tumor promotion. Carcinogenesis September; 1996 17 (9): 2053-9.
29. Soler M N, et al, Gene therapy of rat medullary thyroid cancer by naked nitric oxide synthase II DNA injection. J Gene Med September-October; 2000 2(5): 433-52. and sinusoidal cytotoxicity: a natural hepatic defense against metastasis. Cancer Res Oct. 15, 200060 (20): 5862-9.
30. Wang H H, B 16 melanoma cell arrests in mouse liver induces nitric oxide release and sinusoidal cytotoxicity: a natural hepatic defense against metastasis. Cancer Res Oct. 15, 200060(20): 5862-9.
31. Brennan P A., The action and interactions of nitric oxide in solid tumors. Eur J Surg Oncol Aug. 26, 2000 (5): 434-7.
32. Rieder J, et al. Different patterns of inducible nitric oxide synthase gene expression in ovarian carcinoma cell lines. Anticancer Res September-October; 2000 20(5A): 3251-8.

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

What I claim is:

1. A method for treating nicotine addiction in mammals characterized by abnormally low levels of inflammatory agents by up-regulating indigenous in vivo levels of an inflammatory agent comprising:
   a. contacting the mammalian cells with an inflammatory regulator, comprising at least 2.8 mg pyruvate, or its' salts;
   b. or a pyruvate precursor selected from the group consisting of pyruvyl-glycine, pyruvyl-alanine, pyruvyl-leucine, pyruvyl-valine, pyruvyl-isoleucine, pyruvyl-phenylalanine, pyruvamide, and mixtures thereof; and
   c. wherein said inflammatory agents are selected from the group consisting of elastase, white blood cells, tumor necrosis factor-a and cytokines which are selected from the group consisting of interleukin-6, interleukin-8, interleukin-10, interleukin-17, and interleukin-23.

2. The method of claim 1 wherein the pyruvate and its' salts are selected from the group consisting of pyruvic acid, lithium pyruvate, sodium pyruvate, potassium pyruvate, magnesium pyruvate, calcium pyruvate, zinc pyruvate, manganese pyruvate, aluminum pyruvate, ammonium pyruvate, and mixtures thereof.

3. The method of claim 1 wherein the dosage of the inflammatory regulator ranges from about 2.8 mg to about 1.0 gram.

4. The method of claim 1 further comprising contacting the mammalian cells with a therapeutic agent of nicotine.

5. The method of claim 4, wherein the therapeutic agent is administered prior to delivery of the inflammatory regulator.

6. The method of claim 4, wherein the therapeutic agent is administered concomitantly with delivery of the inflammatory regulator.

7. The method of claim 4, wherein the therapeutic agent is administered after delivery of the inflammatory regulator.

* * * * *